United States Patent
Cichewicz et al.

(10) Patent No.: US 7,132,403 B2
(45) Date of Patent: *Nov. 7, 2006

(54) ANTIHELMINTHIC ANTHRAQUINONES AND METHOD OF USE THEREOF

(75) Inventors: Robert H. Cichewicz, Santa Cruz, CA (US); Muraleedharan G. Nair, Okemos, MI (US); James H. McKerrow, San Francisco, CA (US)

(73) Assignees: Board of Trustees of Michigan State University, East Lansing, MI (US); Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/761,071

(22) Filed: Jan. 20, 2004

(65) Prior Publication Data

US 2004/0152645 A1 Aug. 5, 2004

Related U.S. Application Data

(62) Division of application No. 10/317,906, filed on Dec. 12, 2002, now Pat. No. 6,800,615.

(60) Provisional application No. 60/389,368, filed on Jun. 17, 2002, provisional application No. 60/372,576, filed on Apr. 15, 2002.

(51) Int. Cl.
*A61K 31/70* (2006.01)
*A61K 31/675* (2006.01)
*C07H 15/00* (2006.01)
*C07C 50/18* (2006.01)

(52) U.S. Cl. .................. 514/33; 514/83; 514/510; 514/538; 536/18.1; 552/208; 552/243; 552/261; 552/262; 552/265; 552/266; 552/267

(58) Field of Classification Search .............. 536/18.1; 552/208, 243, 261, 262, 265, 266, 267; 514/33, 514/83, 510, 548, 538
See application file for complete search history.

(56) References Cited

U.S. PATENT DOCUMENTS

| | | |
|---|---|---|
| 4,117,156 A | 9/1978 | Loewe et al. |
| 5,091,385 A | 2/1992 | Gulliya et al. |
| 5,177,073 A | 1/1993 | Gulliya et al. |
| 5,489,590 A | 2/1996 | Gulliya et al. |
| 6,875,746 B1 * | 4/2005 | Nair et al. ............ 514/33 |

OTHER PUBLICATIONS

Chemical Abstracts, 130-1100478 (1998).*
Chemical Abstracts, 120: 212583 (1994).*
Chitsula et al., Acta Trop. 77: 41-51 (2000).
Bica et al., Infect. Dis. Clin. N. Am. 14: 637-642 (2000).
Elliot, Gastroenterol. Clin. N. Am. 25: 599-624 (1996).
Morris and Knauer, Sem. Respir. Infect. 12: 159-170 (1997).
Schafer and Hale, Curr. Gastroenterol. Reports 3: 293-303 (2001).
Cioli, Parasitol. Today 14: 418-422 (1998).
Curr. Opin. Infect Dis. 13: 659-663 (2000).
William et al., Parasitol. 122: 63-66 (2001).
Shiao et al., Acta Pharma. Sinica 9: 218-224 (1962).
Wang et al., Phytochem. 28: 1825-1826 (1989).
Main et al., Aust. Vet. J. 57: 132-135 (1981).
Colegate et al., Aust. J. Chem. 38: 1233-1241 (1985).
Chen et al., Acta. Pharma. Sinica 9: 579-586 (1962).
Khan et al., In Synthesis 255-257 (1994).
Cameron et al., In Tetrahedron Letters 27: 4999-5002 (1986).
Baker and Myers, Pharmacol. Res. 8: 763-770 (1991).
Danielsen and Aksnes, Magn. Reson. Chem. 30: 359-360 (1992).
Schripsema et al., Phytochem. /51: 55-60 (1999).
Li and McLaughlin, J. Nat. Prod. 52: 660-662 (1989).
Midiwo and Arot., Int. J. BioChemiPhysics 2: 115-116 (1993).
Brauers et al., J. Nat. Prod. 63: 739-745 (2000).
Li et al., J. Nat. Prod. 63: 653-656 (2000).
Batterham et al., Aust. J. Chem. 14: 637-642 (1961).
Milovanovic et al., J. Serb. Chem. Soc. 61: 423-429 (1996).
Salter et al., J. Biol. Chem. 275: 38667-38673 (2000).

* cited by examiner

*Primary Examiner*—Elli Peselev
(74) *Attorney, Agent, or Firm*—Ian C. McLeod; Steven E. Merritt

(57) ABSTRACT

Anthraquinones are described which are antihelminthic and in particular, are useful in compositions for inhibiting *Schistosoma* sp. in vitro or in vivo. The preferred anthraquinones have the formula:

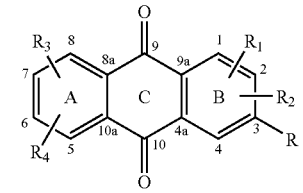

wherein $R_1$, $R_2$, $R_3$, and $R_4$ are each hydrogen, hydroxy, halogen, alkyl, substituted alkyl, alkene, substituted alkene, alkyne, aryl, substituted aryl, cyclic, substituted cyclic, acid group, carbohydrate, or combination thereof, R is a group containing 1 to 12 carbons such as methyl, alkyl, substituted alkyl, aldehyde, hydroxy, hydroxymethyl, acid group, carbohydrate, or combination thereof, and the halogen is I, F, Br, or Cl.

8 Claims, 7 Drawing Sheets

1 $R_1$=H, $R_2$=CH$_3$, $R_3$=H
1a $R_1$=Ac, $R_2$=CH$_3$, $R_3$=H
2 $R_1$=H, $R_2$=H, $R_3$=CH$_3$
2a $R_1$=Ac, $R_2$=H, $R_3$=CH$_3$

3 R=H
4 R=β-D-glucopyranoside
5 R=malonyl-(1→6)-
β-D-glucopyranoside

6 R=H
7 R=β-D-glucopyranoside

8 R=H
9 R=CH$_3$

10 R=H
11 R=OH

12

ANTIHELMINTHIC ANTHRAQUINONES AND METHOD OF USE THEREOF

CROSS-REFERENCE TO RELATED APPLICATION

This application is a divisional of U.S. application U.S. Ser. No. 10/317,906, filed Dec. 12, 2002, now U.S. Pat. No. 6,800,615 which claims priority to Provisional Application Ser. No. 60/372,576, filed Apr. 15, 2002, and Provisional Application Ser. No. 60/389,368, filed Jun. 17, 2002.

STATEMENT REGARDING FEDERALLY SPONSORED RESEARCH OR DEVELOPMENT

Not applicable.

REFERENCE TO A "COMPUTER LISTING APPENDIX SUBMITTED ON A COMPACT DISC"

Not Applicable.

BACKGROUND OF THE INVENTION (1) Field of the Invention

The present invention relates to anthraquinones which are antihelminthic and in particular, are useful in compositions for inhibiting *schistosoma* sp. in vitro or in vivo. The preferred anthraquinones have the formula:

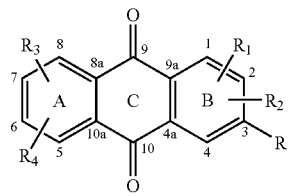

wherein $R_1$, $R_2$, $R_3$, and $R_4$ are each hydrogen, hydroxy, halogen, alkyl, substituted alkyl, alkene, substituted alkene, alkyne, aryl, substituted aryl, cyclic, substituted cyclic, acid group, carbohydrate, or combination thereof, R is a group containing 1 to 12 carbons such as methyl, alkyl, substituted alkyl, aldehyde, hydroxy, hydroxymethyl, acid group, carbohydrate, or combination thereof, and the halogen is I, F, Br, or Cl. In a particular embodiment, the anthraquinones have the formula

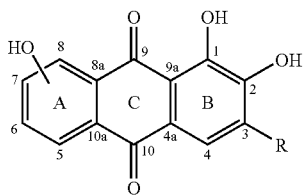

wherein R is a group containing 1 to 12 carbons such as methyl, alkyl, substituted alkyl, aldehyde, hydroxy, hydroxymethyl, acid group, carbohydrate, and combinations thereof.

(2) Description of Related Art

Schistosomasis is a disease caused by parasitic digenetic trematodes of the genus *Schistosoma* that afflicts at least 200 million people worldwide with another 600 million at risk (Chitsula et al., Acta Trop. 77: 41–51 (2000)). Chronic *Schistosoma* infection can lead to the development of a variety of conditions including diarrhea, hepatic fibrosis and portal hypertension, central nervous system disease, embolisms of the pulmonary arterioles, and hematuria. While a large number of schistosomes are known, only five appear to be primarily responsible for human infections including *Schistosoma mansoni, Schistosoma japonicum, Schistosoma mekongi, Schistosoma intercalatum,* and *Schistosoma haematobium*.

These digenetic schistosomes have a complex life-cycle in which free-swimming cercariae emerge from intermediate freshwater snail hosts and infect humans by attaching to the skin via an oral sucker or mucus secretion and penetrate the dermis by releasing proteolytic enzymes. Concurrently, the cercariae shed their tails and transform into schistosomula that enter the venous vascular system where they are carried to the heart and lungs before reaching the systemic circulation. Ultimately, the schistosomula arrive at the liver where they grow into sexually mature adults. Male and female adults form copulating pairs that migrate down the portal vein, eventually reaching the mesenteric or vesical veins, depending on the specific species of schistosome, and begin laying eggs for a period of typically 3 to 5 years. The eggs are generally responsible for triggering the host's immune response that results in the formation of granulomas that lead to the sequelae of clinical manifestations (Bica et al., Infect. Dis. Clin. N. Am. 14: 637–642 (2000); Elliot, Gastroenterol. Clin. N. Am. 25: 599–624 (1996); Morris and Knauer, Sem. Respir. Infect. 12: 159–170 (1997); Schafer and Hale, Curr. Gastroenterol. Reports 3: 293–303 (2001)).

There are limited options available for the chemotherapeutic treatment for *Schistosoma* infections with the drug-of-choice being the pyrazionoisoquinoline, praziquantel (Elliot, ibid.). Unfortunately, the long-term worldwide application of the drug coupled with the recent discovery of praziquantel-tolerant schistosomes has generated concern over the development of drug-resistant *Schistosoma* strains (Cioli, Parasitol. Today 14: 418–422 (1998) and Curr. Opin. Infect Dis. 13: 659–663 (2000); William et al., Parasitol. 122: 63–66 (2001)). With few other options available for combating schistosomiasis, there is an urgent need to develop new methodologies for the treatment and prevention of *Schistosoma* infection (Cioli, ibid.).

Daylily roots (*Hemerocallis* spp., *Hemerocallidaceae*) have been used in Asia to treat schistosomiasis (Shiao et al., Acta Pharma. Sinica 9:218–224 (1962); Shiao et al., Acta Pharma. Sinica 9: 217–224 (1962)). However, this method of treatment has been disfavored due to a host of toxic side effects and deaths associated with the administration of *Hemerocallis* root extracts to humans (Wang et al., Phytochem. 28: 1825–1826 (1989)). Previous efforts to identify the active constituent responsible for the therapeutic properties of *Hemerocallis* roots lead to isolation of a neurotoxic binaphthalenetetrol known as stypandrol (Wang and Yang, 1993) which had been shown to cause paralysis, blindness and death in mammals (Main et al., Aust. Vet. J. 57: 132–135 (1981); Colegate et al., Aust. J. Chem. 38: 1233–1241 (1985)). In another report by Chen et al. (Acta Pharma. Sinica 9: 579–586 (1962)), researchers obtained a yellow powdery isolate to which the authors ascribed both the biological activity against schistosomes, as well as, the toxic side effects associated with the use of *Hemerocallis* roots;

however, its structure was never identified. While other studies have described additional compounds found in daylilies, none of these efforts have addressed the need to fully characterize the bioactive schistosomicidal chemical constituents from *Hemerocallis* roots.

Compounds which have antihelminthic activity are known in the prior art such as oxamniquine, metrifonate, and 4-(4-nitroanilino)-phenylisothiocyanate, which are disclosed in U.S. Pat. No. 4,117,156 to Loewe et al. However, oxamniquine is only effective against *Schistosoma mansoni*, is more active against male rather than female worms, and has little effect on immature worms, and metrifonate is only active against *Schistosoma haematobium*. U.S. Pat. Nos. 5,091,385, 5,177,073, and 5,489,590 to Gulliya et al. disclose a therapeutic mixture comprising a photoactive compound which is capable of killing tumors, bacteria, viruses, and parasites such as *Schistosoma* when activated prior to use with an activating agent such as a chemical, radiation (preferably, irradiation with a laser), gamma rays, or electrons from an electropotential device. The photoactive compounds include a general suggestion of anthraquinones.

In light of the above, there remains a need for novel compounds with antihelminthic activity to increase the arsenal of drugs for combating helminthic infections in warm-blooded animals, including humans.

SUMMARY OF THE INVENTION

The present invention provides a method for inhibiting helminths such as those comprising the *Schistosoma* genus in vivo or in vitro by exposing the helminths to an inhibitory amount of one or more anthraquinones. The anthraquinones can be substituted with halogens such as I, F, Br, and Cl in the ring, particularly where hydroxyl groups are not located. The substituents in the ring can also include one or more of the halogens.

As used herein, the term "inhibitory" means either to limit the growth of the helminth or cells, to stop the growth of the helminth or cells, or to kill the helminth or cells. Thus, the term embraces any affect which adversely affects the helminth or cells.

Therefore, in one embodiment, the present invention provides a method for inhibiting a parasitic helminth which comprises exposing the helminth to an inhibitory amount of an anthraquinone.

In particular, the present invention provides a method for inhibiting a parasitic helminth, which comprises exposing the helminth to an antihelminthic amount of at least one anthraquinone which has the formula:

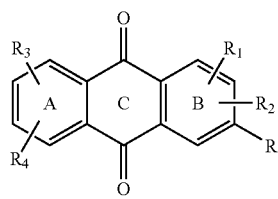

wherein $R_1$, $R_2$, $R_3$, and $R_4$ are each selected from the group consisting of hydrogen, hydroxy, halogen, alkyl, substituted alkyl, alkene, substituted alkene, alkyne, aryl, substituted aryl, cyclic, substituted cyclic, acid group, carbohydrate, and combinations thereof, R is a group containing 1 to 12 carbons selected from the group consisting of methyl, alkyl, substituted alkyl, aldehyde, hydroxy, hydroxymethyl, acid group, carbohydrate, and combinations thereof, and the halogen is selected from the group consisting of I, F, Br, and Cl.

The present invention further provides a method for inhibiting a parasitic helminth, which comprises exposing the helminth to an antihelminthic amount of at least one anthraquinone which has the formula:

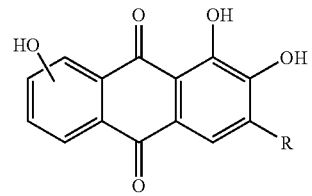

wherein R is a group containing 1 to 12 carbons selected from the group consisting of methyl, alkyl, substituted alkyl, aldehyde, hydroxy, hydroxymethyl, acid group, carbohydrate, and combinations thereof.

The present invention further provides a method for inhibiting a *Schistosoma* sp. which comprises exposing the *Schistosoma* sp. to an inhibitory amount of at least one anthraquinone which has the formula:

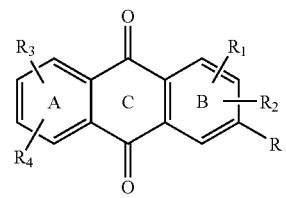

wherein $R_1$, $R_2$, $R_3$, and $R_4$ are each selected from the group consisting of hydrogen, hydroxy, halogen, alkyl, substituted alkyl, alkene, substituted alkene, alkyne, aryl, substituted aryl, cyclic, substituted cyclic, acid group, carbohydrate, and combinations thereof, R is a group containing 1 to 12 carbons selected from the group consisting of methyl, alkyl, substituted alkyl, aldehyde, hydroxy, hydroxymethyl, acid group, carbohydrate, and combinations thereof, and the halogen is selected from the group consisting of I, F, Br, and Cl.

The present invention further provides a method for inhibiting a *Schistosoma* sp. which comprises exposing the *Schistosoma* sp. to an inhibitory amount of at least one anthraquinone of the formula:

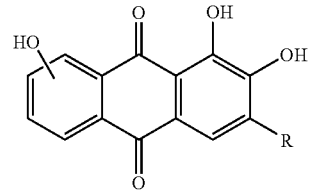

wherein R is a group containing 1 to 12 carbons selected from the group consisting of methyl, alkyl, substituted alkyl, aldehyde, hydroxy, hydroxymethyl, acid group, carbohydrate, and combinations thereof.

In a preferred embodiment of the above methods, the anthraquinone is 1,2,8-trihydroxy-3-methyl anthraquinone (compound 3), 1,2,8-trihydroxy-3-hydroxymethyl anthraquinone (compound 6), or both and the inhibiting can be either in vivo or in vitro.

In a further embodiment of the above methods, the anthraquinone is inhibitory at a dosage of 1 to 1,000 micrograms per milliliter or gram.

The present invention further provides a method for inhibiting a pathogenic trematode in a warm-blooded animal or human infected with the pathogenic trematode comprising (a) providing a composition containing an inhibitory amount of at least one anthraquinone selected from the group consisting of 1,2,8-trihydroxy-3-methyl anthraquinone (compound 3) and 1,2,8-trihydroxy-3-hydroxymethyl anthraquinone (compound 6) in a pharmaceutically acceptable carrier; and (b) and administering the composition to the warm-blooded animal or human to inhibit the pathogenic trematode. A particular composition is a topical composition for swimmers itch which is a species of Schistosoma.

In a further embodiment of the method, the anthraquinone is inhibitory at a dosage of 1 to 1,000 micrograms per milliliter or gram.

In a further still embodiment of the method, the anthraquinone is administered to the warm-blooded animal or human orally, subcutaneously, intraperitoneally, topically, intravenously, topically, intranasally, or rectally.

The present invention further provides a method for inhibiting a pathogenic trematode in a warm-blooded animal or human infected with the pathogenic trematode comprising (a) providing a composition containing an inhibitory amount of 1,2,8-trihydroxy -3-methyl-O-β-D-glucopyranoside anthraquinone (compound 7) and at least one anthraquinone selected from the group consisting of 1,8-dihydroxy-2-O-β-D-glucopyranoside anthraquinone (compound 4) and 1,8-dihydroxy-2-O-malonyl-(1-6)-β-D-glucopyranoside anthraquinone (compound 5) in a pharmaceutically acceptable carrier; and (b) and administering the composition to the warm-blooded animal or human to inhibit the pathogenic trematode.

In a further embodiment of the method, the composition further includes an inhibitory amount of at least one anthraquinone selected from the group consisting of 1,2,8-trihydroxy-3-methyl anthraquinone (compound 3) and 1,2,8-trihydroxy-3-hydroxymethyl anthraquinone (compound 6).

In a further still embodiment of the method, the anthraquinone is inhibitory at a dosage of 1 to 1,000 micrograms per milliliter or gram.

In a still further embodiment, the anthraquinone is administered to the warm-blooded animal or human orally, subcutaneously, intraperitoneally, topically, intranasally, intravenously, or rectally.

In a preferred embodiment of the above methods, the anthraquinone is selected from the group consisting of 1-hydroxy-2-acetyl-3,6-methyl anthraquinone (compound 1), 2-acetyl-3,6-methyl anthraquinone monoacetate (compound 1a), 1-hydroxy-2-acetyl -3,7-methyl anthraquinone (compound 2), 2-acetyl -3,7-methyl anthraquinone monoacetate (compound 2a), 1,2,8-trihydroxy-3-methyl anthraquinone (compound 3), 1,8-dihydroxy-2-O-β-D-glucopyranoside anthraquinone (compound 4), 1,2,8-trihydroxy-3-hydroxymethyl anthraquinone (compound 6), and 1,8-dihydroxy-3-carboxy anthraquinone (compound 8) and the inhibiting can be either in vivo or in vitro.

In a further embodiment of the above methods, the anthraquinone is inhibitory at a dosage of 1 to 1,000 micrograms per milliliter or gram.

The present invention further provides an antihelminthic composition which comprises (a) at least one anthraquinone which has the formula:

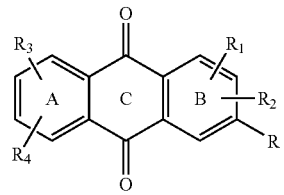

wherein $R_1$, $R_2$, $R_3$, and $R_4$ are each selected from the group consisting of hydrogen, hydroxy, halogen, alkyl, substituted alkyl, alkene, substituted alkene, alkyne, aryl, substituted aryl, cyclic, substituted cyclic, acid group, carbohydrate, and combinations thereof, R is a group containing 1 to 12 carbons selected from the group consisting of methyl, alkyl, substituted alkyl, aldehyde, hydroxy, hydroxymethyl, acid group, carbohydrate, and combinations thereof, and the halogen is selected from the group consisting of I, F, Br, and Cl; and (b) a pharmaceutically acceptable carrier, preferably wherein the composition contains between about 1 and 1,000 micrograms of the anthraquinone per milliliter or gram of the carrier.

Preferably, the anthraquinone has the formula:

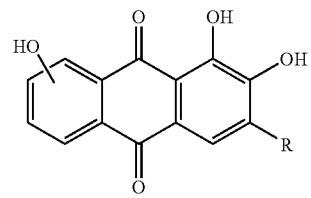

wherein R is a group containing 1 to 12 carbons selected from the group consisting of methyl, alkyl, substituted alkyl, aldehyde, hydroxy, hydroxymethyl, acid group, carbohydrate, and combinations thereof.

More preferably, the anthraquinone is selected from the group consisting of 1-hydroxy-2-acetyl -3,6-methyl anthraquinone (compound 1), 2-acetyl-3,6-methyl anthraquinone monoacetate (compound 1a), 1-hydroxy-2-acetyl-3,7-methyl anthraquinone (compound 2), 2-acetyl-3,7-methyl anthraquinone monoacetate (compound 2a), 1,2,8-trihydroxy-3-methyl anthraquinone (compound 3), 1,8-dihydroxy-2-O-β-D-glucopyranoside anthraquinone (compound 4), 1,2,8-trihydroxy-3-hydroxymethyl anthraquinone (compound 6), and 1,8-dihydroxy-3-carboxy anthraquinone (compound 8).

The present invention also provides an isolated and purified anthraquinone which has the formula:

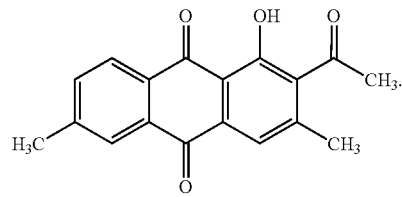

The present invention also provides an isolated and purified anthraquinone which has the formula:

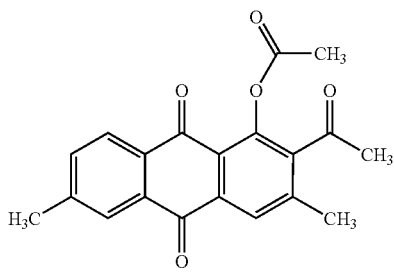

The present invention also provides an isolated and purified anthraquinone which has the formula:

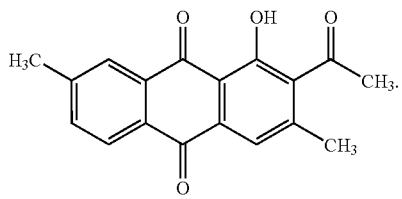

The present invention also provides an isolated and purified anthraquinone which has the formula:

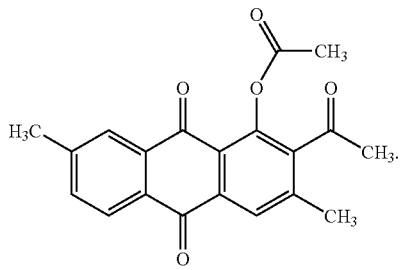

The present invention also provides an isolated and purified anthraquinone which has the formula:

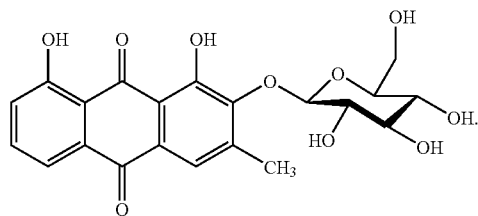

The present invention also provides an isolated and purified anthraquinone which has the formula:

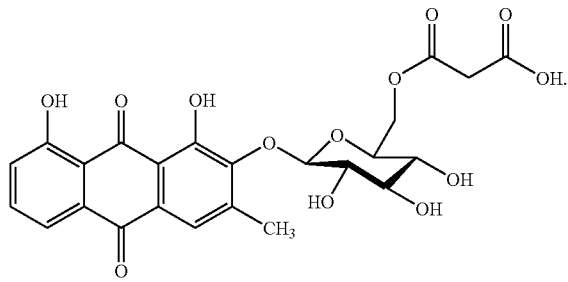

The present invention also provides an isolated and purified anthraquinone which has the formula:

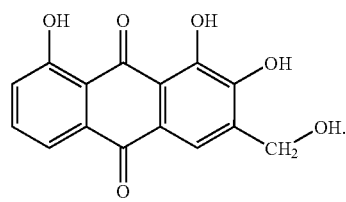

The present invention also provides an isolated and purified anthraquinone which has the formula:

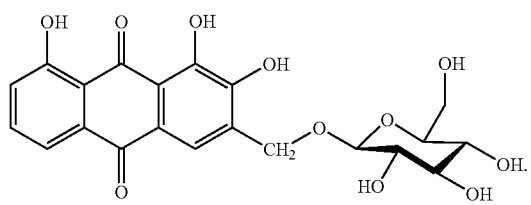

The present invention also provides an isolated and purified anthraquinone which has the formula:

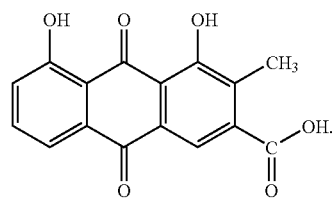

OBJECTS

Therefore, it is an object of the present invention to provide compositions such as the anthraquinones disclosed herein which have antihelminthic activity.

It is further an object of the present invention to provide methods for using the anthraquinones to inhibit helminths infecting warm-blooded animals, including humans.

Further still, it is an object of the present invention to provide methods for using the anthraquinones to inhibit pathogenic trematodes such as those of the *Schistosoma* genus infecting warm-blooded animals, including humans.

These and other objects of the present invention will become increasingly apparent with reference to the following drawings and preferred embodiments.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The present invention provides anthraquinones and methods for their use as antihelminthic compounds to combat helminthic infections of warm-blooded animals, including humans. In particular, the anthraquinones are hydroxyanthraquinones, which along with anthraquinones in general, are believed to be unknown in the prior art as being useful per se for antihelminthic applications. Hydroxy-substituted anthraquinones can be derived synthetically as described by Khan et al., in Synthesis 255–257 (1994) and by Cameron et al. in Tetrahedron Letters 27: 4999–5002 (1986) or can be isolated from plant sources such as the roots of daylilies (*Hemerocallis fulva*) as described hereinafter.

Figure 1:
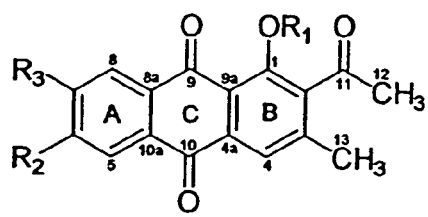
FIG. 1 is a chart showing the chemical structure of compounds 1 to 12 isolated from daylily roots of *Hemerocallis fulva* "Kwanzo" Kaempfer (1712). Ac refers to acetyl groups such as —COCH$_3$.
Figure 1:
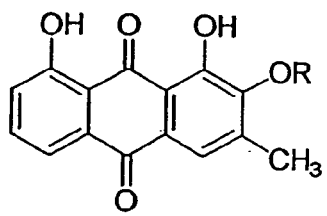
Figure 1:
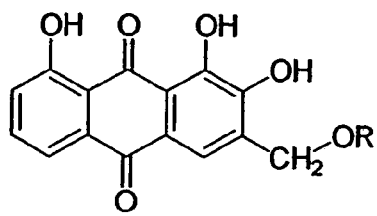
Figure 1:
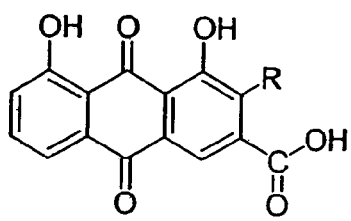
Figure 1:
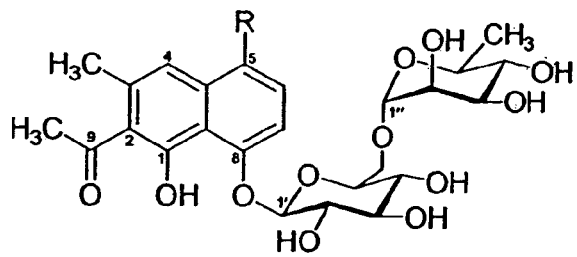
Figure 1:
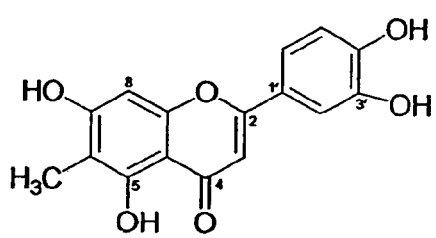

As described herein in the Examples, the roots of *H. fulva* (Kwanzo) were extracted with hexane, EtOAc, and MeOH. The hexane and MeOH extracts were selected for further study and subsequently subjected to a combination of chromatographic procedures including Si gel MPLC and PTLC, ODS MPLC and preparative HPLC, and crystallization. This led to the discovery and isolation of nine novel anthraquinones, the kwanzoquinones: kwanzoquinone A (compound 1: (1-hydroxy-2-acetyl-3,6-methyl anthraquinone), kwanzoquinone A monoacetate (compound 1a: (2-acetyl-3,6-methyl anthraquinone monoacetate), kwanzoquinone B (compound 2: (1-hydroxy-2-acetyl-3,7-methyl anthraquinone), kwanzoquinone B monoacetate (compound 2a: (2-acetyl-3,7-methyl anthraquinone monoacetate), kwanzoquinone C (compound 4: (1,8-dihydroxy -2-O-β-D-glucopyranoside anthraquinone), kwanzoquinone D (compound 5: (1,8-dihydroxy-2-malonyl -(1→6)-O-β-D-glucopyranoside anthraquinone), kwanzoquinone E (compound 6: (1,2,8-trihydroxy-3-hydroxymethyl anthraquinone), kwanzoquinone F (compound 7: (1,2,8-trihydroxy-3-methyl-O-β-D-glucopyranoside anthraquinone), and kwanzoquinone G (compound 9: (1,8-dihydroxy-2-methyl-3-carboxy anthraquinone) and a novel naphthalene glycoside (compound 11; 5-hydroxydianellin). The structures and complete $^1$H and $^{13}$C NMR spectral assignments for these novel compounds, as well as those for known compounds 3 (an anthraquinone known as 1,2,8-hydroxy-3-methylanthraquinone or 2-hydroxychrysophanol), 10 (dianellin), and 12 (6-methylluteolin), were made based on thorough 1D and 2D NMR studies and are disclosed herein for the first time. The structures of the above compounds are shown in FIG. 1. The anthraquinones are soluble in a variety of protic and aprotic solvents including, but not limited to, DMSO, alcohols such as ethanol, aqueous alkali hydroxide solutions, $Na_2CO_3$ solutions, and $NH_3$ solutions.

When the anthraquinones were tested for antihelminthic activity, it was discovered that compounds 3 and 6 had antihelminthic activity. Compound 3 at a concentration of about 25 μg/mL was found to rapidly immobilize *Schistosoma* cercariae within about 15 seconds of exposure and to kill about 50% of the cercariae by 24 hours post-exposure. At a concentration of about 3.125 μg/mL, the cercariae were immobilized within about 45 minutes of exposure. Compound 6 at a concentration of about 25 μg/mL was also found to immobilize the cercariae but over a time frame of about 12 to 14 minutes. However, compound 6 killed all of the cercariae by 24 hours post-exposure. Compounds 4 and 5 are hydrolyzable to compound 3 and compound 7 is hydrolyzable to compound 6. These results demonstrate that the anthraquinones, particularly compounds 3 and 6, have different modes of action but that both are useful to treat helminthic infections either separately or in combination.

Therefore, the anthraquinones of the present invention, which are useful as antihelminthic compounds, include both the particular anthraquinones compounds with the antihelminthic activity per se and anthraquinones compounds which are hydrolyzed in the gut of the helminth or warm-blooded animal, including humans, or hydrolyzed in vitro to produce the compounds with the antihelminthic activity. For example, anthraquinones with sugar substituents (compounds 4, 5, and 7) can be hydrolyzed in the gut of the helminth or warm-blooded animals, including humans, to which the compounds are administered to produce the anthraquinones with antihelminthic activity.

The anthraquinones are particularly useful in a method of treatment for inhibiting helminths, particularly those helminths which are important in human medicine. Such helminths include those which reside in the intestinal tract such as hookworms, particularly *Ancyclostoma* or *Necator*, and those which reside in the bloodstream such as the parasitic digenetic trematodes of the genus *Schistosoma*, particularly *Schistosoma haematobium*, *Schistosoma mansoni*, *Schistosoma mekongi*, *Schistosoma intercalatum*, and *Schistosoma japonicum*.

The anthraquinones which have antihelminthic activity and, therefore, are useful as antihelminthic compounds have the following general chemical formula:

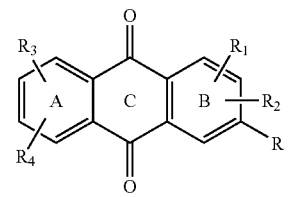

wherein $R_1$, $R_2$, $R_3$, and $R_4$ are each selected from the group consisting of hydrogen, hydroxy, halogen, alkyl, substituted alkyl, alkene, substituted alkene, alkyne, aryl, substituted aryl, cyclic, substituted cyclic, acid group, carbohydrate, and combinations thereof, R is a group containing 1 to 12 carbons selected from the group consisting of methyl, alkyl, substituted alkyl, aldehyde, hydroxy, hydroxymethyl, acid group, carbohydrate, and combinations thereof, and the halogen is selected from the group consisting of I, F, Br, and Cl.

In a particular embodiment, the anthraquinones have the following general chemical structure:

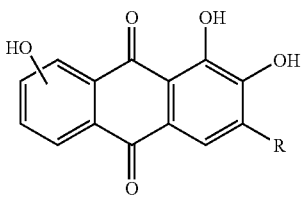

wherein R is a group containing 1 to 12 carbons selected from the group consisting of methyl, alkyl, substituted alkyl, aldehyde, hydroxy, hydroxymethyl, acid group, carbohydrate, and combinations thereof.

The preferred anthraquinones with antihelminthic activity with the above general chemical formula are 1,2,8-trihydroxy-3-methylanthraquinone, which is compound 3 isolated from daylilies and which has the trivial name 2-hydroxychrysophanol, and which has the chemical formula:

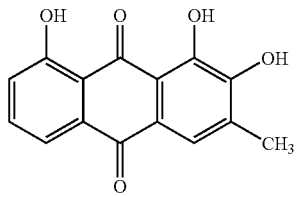

and 1,2,8-trihydroxy-3-hydroxymethylanthraquinone, which is novel compound 6 isolated from daylilies and which has been given the trivial name kwanzoquinone F, and which has the chemical formula:

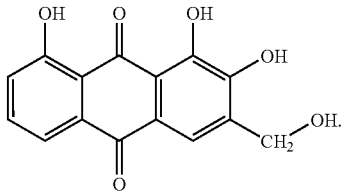

Anthraquinones which can be hydrolyzed in vitro or in vivo such as in the gut of helminths or warm-blooded animals or humans to anthraquinones with antihelminthic activity are also useful as antihelminthic compounds. These anthraquinones have the general chemical formula A:

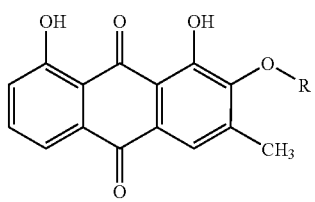

or the general chemical formula B:

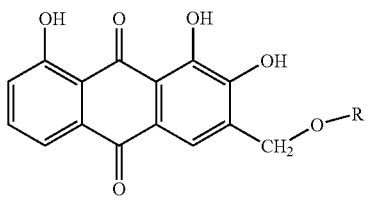

wherein for each, R is selected from the group consisting of lower alkyl, lower substituted alkyl containing 1 to 12 carbon atoms, an aldehyde group, a carbohydrate, and an acid group.

The preferred anthraquinones which can be hydrolyzed to anthraquinones with antihelminthic activity with the general chemical formula A include 1,8-dihydroxy-2-O-β-glucopyranoside-3-methylanthraquinone, which is novel compound 4 isolated from daylilies and which has been given the trivial name kwanzoquinone D, and which has the chemical formula:

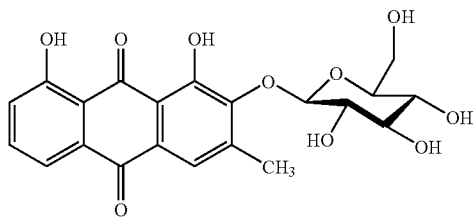

and 1,8-dihydroxy-2-O-β-D-glucopyranoside((1→6) malonyl)-3-methylanthraquinone, which is novel compound 5 isolated from daylilies and which has been given the trivial name Kwanzoquinone E, and which has the chemical formula:

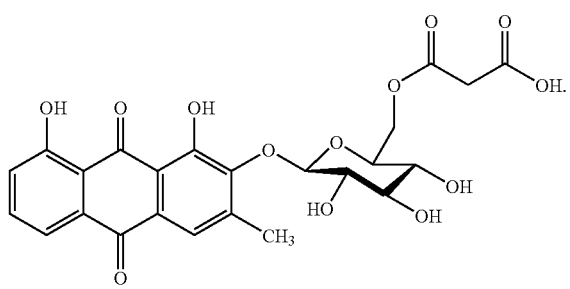

The preferred anthraquinone which can be hydrolyzed to a anthraquinone with antihelminthic activity with the general chemical formula B is 1,2,8-trihydroxy -3-methyl-O-β-D-glucopyranoside-anthraquinone, which is novel compound 7 isolated from daylilies and which has been given the trivial name kwanzoquinone F, and which has the chemical formula:

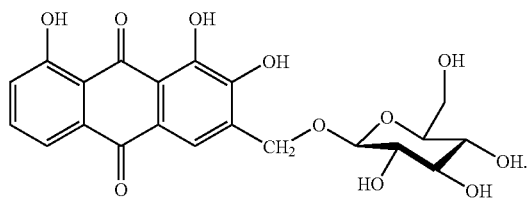

As is evident from the chemical formulas for compound 4 and 5, when either compound is hydrolyzed in vivo or in vitro, it is hydrolyzed to compound 3. When compound 7 is hydrolyzed in vivo or in vitro, it is hydrolyzed to compound 6. As shown herein, both compounds 3 and 6 have antihelminthic activity.

The method for treating a warm-blooded animal or human infected with a helminth (patient), in particular a pathogenic trematode such as *Schistosoma* sp., comprises providing to the warm-blooded animal or human an antihelminthic composition comprising as the active ingredient an inhibitory amount of one or more of the anthraquinones, preferably one or more anthraquinones selected from the group consisting of compounds 3, 4, 5, 6, and 7.

For example, in one embodiment, the warm-blooded animal or human is provided an inhibitory amount of compound 3 or compound 6. In a further embodiment, which is preferred, the warm-blooded animal or human is provided an inhibitory amount of compounds 3 and 6. In an embodiment further still, the warm-blooded animal or human is provided an inhibitory amount of at least one compound selected from the group consisting of compounds 4, 5, and 7. In an embodiment further still, the warm-blooded animal or human is provided an inhibitory amount of compound 7 and inhibitory amount of at least one compound selected from the group consisting of compounds 4 and 5. In an embodiment further still, the warm-blooded animal or human is provided an inhibitory amount of compound 3 and an inhibitory amount of compound 7. In an embodiment further still, the warm-blooded animal or human is provided an inhibitory amount of compound 7 and an inhibitory amount of at least one compound selected from the group consisting of compounds 4 and 5 and an inhibitory amount of at least one compound selected from the group consisting of compounds 3 and 6. It is readily apparent that other embodiments comprising particular combinations of the aforementioned compounds can be used as the active ingredient in antihelminthic compositions for inhibiting helminths, in particular pathogenic trematodes such as those of the *Schistosoma* genus. In the aforementioned compositions, the anthraquinone is inhibitory at a dosage of 1 to 1,000 micrograms per milliliter or gram.

Because the anthraquinones isolated from the day lily are antihelminthic without the need for activation prior to administering to the warm-blooded animal or human, antihelminthic compositions comprising the anthraquinones can include a wide variety of embodiments for administering the anthraquinones, to the warm-blooded animal or human. Furthermore, the antihelminthic compositions can be administered to warm-blooded animals or humans in non-medical environments (outside hospitals and medical clinics) and in environments where access to activating agents is either limited, expensive, or non-existent.

In a preferred embodiment, one or more of the anthraquinones for curing a warm-blooded animal, including humans, of a helminth infection, or inhibiting the infection, are provided to the warm-blooded animal or human at an inhibitory dose in a pharmaceutically acceptable carrier. Therefore, the anthraquinones are processed with pharmaceutical carrier substances by methods well known in the art such as by means of conventional mixing, granulating, coating, suspending and encapsulating methods, into the customary preparations for oral, rectal, or other mode of administration. For example, antihelminthic anthraquinone preparations for oral application can be obtained by combining one or more of the anthraquinones with solid pharmaceutical carriers; optionally granulating the resulting mixture; and processing the mixture or granulate, if desired and/or optionally after the addition of suitable auxiliaries, into the form of tablets or dragee cores.

Suitable pharmaceutical carriers for solid preparations are, in particular, fillers such as sugar, for example, lactose, saccharose, mannitol or sorbitol, cellulose preparations and/or calcium phosphates, for example, tricalcium phosphate or calcium hydrogen phosphate; also binding agents, such as starch paste, with the use, for example, of maize, wheat, rice or potato starch, gelatine, tragacanth, methyl cellulose, hydroxypropylmethyl cellulose, sodium carboxymethyl cellulose and/or polyvinylpyrrolidone, esters of polyacrylates or polymethacrylates with partially free functional groups; and/or, if required, effervescent agents, such as the above-mentioned starches, also carboxymethyl starch, cross-linked polyvinylpyrrolidone, agar, or alginic acid or a salt thereof, such as sodium alginate. Auxiliaries are primarily flow-regulating agents and lubricating agents, for example, silicic acid, talcum, stearic acid or salts thereof, such as magnesium stearate or calcium stearate. Dragee cores are provided with suitable coatings, optionally resistant to gastric juices, whereby there are used, inter alia, concentrated sugar solutions optionally containing gum arabic, talcum, polyvinylpyrrolidone, and/or titanium dioxide, lacquer solutions in aqueous solvents or, for producing coatings resistant to stomach juices, solutions of esters of polyacrylates or polymethacrylates having partially free functional groups, or of suitable cellulose preparations such as acetylcellulose phthalate or hydroxypropylmethylcellulose phthalate, with or without suitable softeners such as phthalic acid ester or triacetin. Dyestuffs or pigments may be added to the tablets or dragee coatings, for example for identification or marking of the various doses of active ingredient.

Further antihelminthic preparations comprising one or more of the anthraquinones which can be administered orally are hard gelatine capsules, as well as hard or soft closed capsules made from gelatine and, if required, a softener such as glycerin or sorbitol. The hard gelatine capsules can contain one or more of the anthraquinones in the form of a granulate, for example in admixture with fillers such as maize starch, optionally granulated wheat starch, binders or lubricants such as talcum, magnesium stearate or colloidal silicic acid, and optionally stabilizers. In closed capsules, the one or more of the anthraquinones is in the form of a powder or granulate; or it is preferably present in the form of a suspension in suitable solvent, whereby for stabilizing the suspensions there can be added, for example, glycerin monostearate.

Other antihelminthic preparations to be administered orally are, for example, aqueous suspensions prepared in the usual manner, which suspensions contain the one or more of the anthraquinones in the suspended form and at a concentration rendering a single dose sufficient. The aqueous suspensions either contain at most small amounts of stabilizers and/or flavoring substances, for example, sweetening agents such as saccharin-sodium, or as syrups contain a certain amount of sugar and/or sorbitol or similar substances. Also suitable are, for example, concentrates or concentrated suspensions for the preparation of shakes. Such concentrates can also be packed in single-dose amounts.

Suitable antihelminthic preparations for rectal administration are, for example, suppositories consisting of a mixture of one or more of the anthraquinones with a suppository foundation substance. Such substances are, in particular, natural or synthetic triglyceride mixtures. Also suitable are gelatine rectal capsules consisting of a suspension of the one or more of the anthraquinones in a foundation substance. Suitable foundation substances are, for example, liquid triglycerides, of higher or, in particular, medium saturated fatty acids.

Likewise of particular interest are preparations containing the finely ground one or more of the anthraquinones, preferably that having a median of particle size of 5 µm or less, in admixture with a starch, especially with maize starch or wheat starch, also, for example, with potato starch or rice starch. They are produced preferably by means of a brief mixing in a high-speed mixer having a propeller-like, sharp-edged stirring device, for example with a mixing time of between 3 and 10 minutes, and in the case of larger amounts of constituents with cooling if necessary. In this mixing process, the particles of the one or more of the anthraquinones are uniformly deposited, with a continuing reduction of the size of some particles, onto the starch particles. The mixtures mentioned can be processed with the customary, for example, the aforementioned, auxiliaries into the form of solid dosage units; i.e., pressed for example into the form of tablets or dragees or filled into capsules. They can however also be used directly, or after the addition of auxiliaries, for example, pharmaceutically acceptable wetting agents and distributing agents, such as esters of polyoxyethylene sorbitans with higher fatty acids or sodium lauryl sulphate, and/or flavoring substances, as concentrates for the preparation of aqueous suspensions, for example, with about 5- to 20-fold amount of water. Instead of combining the anthraquinone/starch mixture with a surface-active substance or with other auxiliaries, these substances may also be added to the water used to prepare the suspension. The concentrates for producing suspensions, consisting of the one or more of the anthraquinones/starch mixtures and optionally auxiliaries, can be packed in single-dose amounts, if required in an airtight and moisture-proof manner.

In addition, the antihelminthic preparations can be administered intraperitoneally, intranasally, subcutaneously, or intravenously. In general, for intraperitoneal, intranasal, subcutaneous, or intravenous administration, one or more of the antihelminthic antroquinones are provided by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the one or more antihelminthic anthraquinones are provided in a composition acceptable for intraperitoneal, subcutaneous, or intravenous use in warm-blooded animals, and humans in particular.

Antihelminthic preparations according to the present invention comprise one or more of the anthraquinones at a concentration suitable for administration to warm-blooded animals, and humans in particular, which concentration is, depending on the mode of administration, between about 0.3% and 95%, preferably between about 2.5% and 90%. In the case of suspensions, the concentration is usually not higher than 30%, preferably about 2.5%; and conversely in the case of tablets, dragees and capsules with the one or more of the anthraquinones, the concentration is preferably not lower than about 0.3%, in order to ensure an easy ingestion of the required doses of the one or more anthraquinones. The treatment of warm-blooded animals or humans infested with parasitic helminths with the preparations comprising one or more of the anthraquinones is carried out preferably by a single oral, rectal, intraperitoneal, intranasal, subcutaneous, or intravenous administration of an amount which contains a dose of the one or more anthraquinones sufficient to practically completely free the warm-blooded animal or human from the parasitic helminths, that is to say, an amount which is sufficient of cure the warm-blooded animal or human of the infection caused by the parasitic helminths or inhibit the growth of the parasitic helminth in the warm-blooded animal or human. If required, this curative dose can be divided into several partial doses which are administered at intervals of several hours to several days. The administered dose of the one or more anthraquinones, is dependent both on the species and general condition of the warm-blooded animal or human to be treated and on the genus and species of the helminths infecting the warm-blooded animal or human.

The anthraquinones are useful for curing warm-blooded animals and humans of infections, or inhibiting the infections, of *Ascaridia galli, Trichostrongylidae,* for example, *Nippostrongylus brasiliensis* or *Nematospiroides dubius, Ancylostomatidae,* for example, *Necator americanus* and *Ancylostoma ceylanicum,* and *Strongylidae;* against *Cestoda* such as *Hymenolepsis nana, Anoplocephalidae* and *Taeniidae;* and particularly against *Trematoda* such as *Fasciolida,* for example, *Fasciola hepatica,* and particularly *Schistosoma,* for example, *Schistosoma mansoni, Schistosoma japonicum, Schistosoma mekongi, Schistosoma intercalatum,* and *Schistosoma hematobium*; also against the pathogens of filariasis, for example, *Dipetalonema witei* and *Litomosoides carinii.* The antihelminthic preparations according to the invention can be used, therefore, for the treatment of warm-blooded animals and humans in the case of infestation with parasitic helminthes such as the aforementioned, especially for the treatment of warm-blooded animals and humans affected by schistosomiasis, hookworm infestation or filariasis.

The anthraquinones are also useful for treating fresh water to immobilize and/or kill pathogenic helminths, particularly *Schistosoma* cercariae, which are in the water. Thus, the anthraquinones are useful in eradication programs for reducing the number of *Schistosoma* in or eliminating *Schistosoma* from fresh water lakes, ponds, streams, rivers, pools, and the like. In general, a solution comprising one or more of the anthraquinones is applied to body of water by spraying to the surface or by injecting into the body of water below the surface. Alternatively, the one or more anthraquinones are applied to the body of water in a dry form.

The following examples are intended to promote a further understanding of the present invention.

EXAMPLE 1

This example illustrates the extraction and isolation of the kwanzoquinones from daylilies.

*Hemoricallis fulva* (Kwanzo) plants were purchased from the Perennial Patch (Wade, N.C.) in August 1999. The plants were grown on the Michigan State University Campus before being harvested in April 2001. The leaves were removed and the roots and crowns of 124 plants were washed and frozen at −4° C. The frozen roots were lyophilized and ground in a WARING blender yielding 2.2 kg of fine light-brown powder.

For isolation and purification of compounds 1 to 12 involved the use of SEPHADEX LH-20 (Sigma-Aldrich, St. Louis, Mo.), Si gel (particle size 40–63 μm) from Fischer Scientific (Pittsburgh, Pa.), AMBERLITE XAD-16 resin from Supelco (Bellafonte, Pa.), LC-SORB SP-A-ODS gel (particle size 25–40 μm) from Dychrom (Santa Clara, Calif.), and Si gel PTLC plates (20×20 cm; 250, 500, and 1000 μm thick) from Analtech, Inc. (Newark, Del.). Preparative HPLC was performed on a Japan Analytical Industry Co. model LC-20 recycling preparative HPLC with a JAIGEL-C$_{18}$ column (10 μm, 20 mm×250 mm). All solvents and chemicals were purchased from Spectrum Laboratory Products, Inc. (New Brunswick, N.J.) and were of ACS analytical grade.

The lyophilized roots (2.0 kg) were sequentially extracted with 3×8 L portions of hexane ethyl acetate, and methanol yielding 25, 23, and 130 g of extract, respectively. The hexane extract was redissolved in 500 mL of hexane and partitioned with 3×500 mL portions of methanol. The methanol fractions were pooled yielding 15 g of extract which was applied to Si gel VLC and eluted with 4 L hexane, 3 L hexane-acetone (9:1), and 3 L hexane-acetone (3:2). The hexane elute (8.5 g) was subjected to Si gel MPLC under gradient conditions with 100% hexane to 100% acetone and 200 mL fractions were collected. All fractions were analyzed by TLC and pooled according to similarities in their profiles yielding fractions A1 to A4.

The hexane-acetone (9:1) eluate from the Si gel VLC was subjected to Si gel MPLC under gradient conditions with 100% hexane to hexane-acetone (1:1) providing fractions B1 to B4.

Fraction B2 (1.5 g) was rechromatographed by Si gel MPLC under gradient conditions-with 100% hexane to 100% EtOAc and 200 mL fractions were collected and pooled based on TLC profiles giving fractions C1 to C4.

Fractions A3 (1 g), A4 (1 g), C2 (300 mg), and C3 (300 mg) were pooled based further examination by TLC and applied to Si gel MPLC. Elution was carried out under gradient conditions with 100% hexane to 100% CHCl$_3$ to CHCl$_3$-ethanol (1:1) 18 mL fractions D1 to D90 were collected.

Fractions D1 to D10 were pooled (500 mg) and further subjected to Si gel MPLC under gradient conditions with 100% hexane to hexane-acetone (97:3) and 15 mL fractions E1 to E40 were collected.

Fractions E6 to E20 (200 mg) were composed of primarily one major component and thus pooled and subjected to sequential Si gel PTLC with hexane-EtOAc (10:1) (72 mg), hexane-diethyl ether (6:1) (51 mg), and benzene-CHCl$_3$ (20:1) yielding 30 mg of α-tocopherol as a clear oil that exhibited spectral characteristics identical to those reported in the literature (Baker and Myers, Pharmacol. Res. 8: 763–770 (1991)).

Fractions D12 to D45 (300 mg) were combined, applied to Si gel PTLC plates, and developed in benzene-CHCl$_3$ (10:1) twice. A bright yellow band (44 mg) was obtained and following extraction from the Si gel, it was dissolved in a minimal volume of CHCl$_3$ and hexane added drop-wise until a slight degree of turbidity was noted. The solution was stored at −20° C. yielding an inseparable 1:1 mixture (based on $^1$H NMR) of compounds 1 and 2 as fine yellow needles (12 mg). Both compounds 1 and 2 and their mono acetates 1a and 2a (prepared from Ac$_2$O/pyridine) were subjected to a variety of chromatographic techniques including further Si gel TLC and MPLC, as well as, ODS MPLC and ODS preparative HPLC, but failed to separate these two compounds.

The MeOH extract of the roots was dissolved in 800 mL MeOH-H$_2$O (3:1) and left at 4° C. until a precipitate formed. The mixture was centrifuged (16,000×g, 15 min, 4° C.) and the supernatant decanted to give 30 g of extract. This was applied to a column of XAD-16 resin and eluted with 10 L H$_2$O, 6 L 25% aqueous MeOH, and 8 L 100% MeOH. The MeOH eluate (18 g) was dissolved in 500 mL H$_2$0 and partitioned with CHCl$_3$ (3×300 mL). The CHCl$_3$ fractions were pooled and dried yielding 2 g of extract that was applied to ODS MPLC and eluted with 50 to 100% MeOH and 16 mL fractions F1 to F166 were collected. Fractions F116 to F125 were pooled giving 100 mg of residue that was dissolved in MeOH-acetone (3:1) and stored at −20° C. yielding 7 mg of compound 8 as a yellow powder. Compound 8 was identified as rhein based on comparisons of its physical and spectral data to those reported in the literature (Danielsen and Aksnes, Magn. Reson. Chem. 30: 359–360 (1992)).

The aqueous phase (16 g) from partitioning with CHCl$_3$ was dissolved in 50 mL of MeOH and 450 mL of acetone was slowly added while stirring and the mixture left at 4° C. The supernatant (14 g) was applied to ODS MPLC and eluted with 45 to 100% MeOH under gradient conditions yielding 750 mL fractions G1 to G6. Fraction G3 (1 g) was again applied to ODS MPLC and eluted with CH$_3$CN—MeOH—H$_2$0-TFA (25:25:50:0.1 to 30:30:40:0.1) under gradient conditions yielding fractions H1 to H6. Fraction H5 (170 mg) was applied to SEPHADEX LH-20 with MeOH. The major component eluted as a yellow band (25 mg) and was further purified by ODS preparative HPLC with CH$_3$CN—MeOH—H$_2$0-TFA (50:20:30:0.1) yielding 16 mg of compound 9 as a yellow powder.

Fraction G1 (10 g) was applied to ODS MPLC with 10 to 50% CH$_3$CN under gradient conditions and 550 mL fractions 11 to 17 were collected. Fraction 13 (410 mg) was chromatographed on SEPHADEX LH-20 with MeOH yielding 80 mg of yellow amorphous solid. This material was further purified by successive Si gel PTLC chromatography with EtOAc—CHCl$_3$—MeOH—H$_2$0—HCOOH (65:25:10:0.8:0.1) (75 mg) followed by CHCl$_3$—MeOH—H$_2$O (8:2:1) (70 mg). Final purification by ODS preparative HPLC with 60% MeOH gave 61 mg of compound 10 as a clear yellow glass-like solid.

Fraction 14 (1.5 g) was applied to SEPHADEX LH-20 and eluted with MeOH giving 150 mL fractions 11 to 16. Fractions 13 to 16 (400 mg), 17 (300 mg), and H2 to H4 (700 mg) were pooled and subjected to ODS MPLC with CH$_3$CN—MeOH—H$_2$0-TFA (20:20:60:0.1 to 40:40:20:0.1) under gradient conditions and 16 mL fractions K1 to K105 were collected. Fractions K22 to K38 (430 mg) were combined and chromatographed on SEPHADEX LH-20 with MeOH giving fractions L1 to L2. Fraction L1 (300 mg) was applied to Si gel PTLC and developed twice with CHCl$_3$—MeOH—H$_2$0 (8:2:0.1) giving a single band that was further purified by ODS preparative HPLC with 60% MeOH to yield 31 mg of compound 11 as a clear glass-like solid.

Fractions L2 (130 mg) was applied to SEPHADEX LH-20 and eluted with MeOH to give 80 mg of a yellow amorphous solid. This material was dissolved in MeOH and placed at −20° C. yielding 62 mg of precipitate. The precipitate was chromatographed twice by ODS preparative HPLC with CH$_3$CN—MeOH—H$_2$O-TFA (40:15:45:0.1) to give 30 mg of yellow solid. Further purification (preparative HPLC) was achieved using 60 to 100% MeOH under gradient conditions yielding a single fraction that was reduced in vacuo and placed at −20° C. to providing 1 mg of compound 7 as a yellow powder.

Fractions K50 to K55 were combined (98 mg) and subjected to SEPHADEX LH-20 chromatography with MeOH and 125 mL fractions M1 to M5 were collected. Fraction M5 (40 mg) was dissolved in MeOH and left at room temperature whereupon 25 mg of compound 4 was obtained as fine yellow needles.

Fractions K56 to K62 were pooled (130 mg) and applied to SEPHADEX LH-20 with MeOH giving fractions N1 to N3. Fraction N1 (50 mg) was subjected to further SEPHADEX LH-20 chromatography with MeOH giving a fraction (35 mg) that was chromatographed using ODS preparative HPLC with $CH_3CN$—MeOH—$H_2O$-TFA (50:20:30:0.1). A single fraction was collected, reduced in vacuo, and placed at −20° C. yielding 6 mg of compound 5 as golden yellow needles. Fraction N2 (7 mg) was further purified by ODS preparative HPLC with $CH_3CN$—MeOH—$H_2O$-TFA (50:20:30:0.1) providing 1 mg of compound 12 as a yellow glass-like solid.

Fractions K63 to K77 were pooled and subjected to SEPHADEX LH-20 with MeOH and 100 mL fractions 01 to 05). Fraction 03 (30 mg) was applied to ODS preparative HPLC with $CH_3CN$—MeOH—$H_2O$-TFA (50:20:30:0.1) yielding 6 mg of yellow amorphous solid. This material was further purified by ODS preparative HPLC under the same conditions and the resultant fraction reduced in vacuo and placed at −20° C. yielding 4 mg of compound 6 as fine yellow needles.

Fractions K94 to K100 were reduced in vacuo to dryness yielding 13 mg of orange amorphous solid. This material was dissolved in a minimal volume of MeOH and left at −20° C. providing 7 mg of compound 3 as orange needles.

The 12 compounds were obtained in the yields shown in Table 1.

TABLE 1

Yield of the twelve compounds isolated from
H. Fulva "Kwanzo" roots.

| Compound | Yield (mg/kg) | Compound | Yield (mg/kg) |
|---|---|---|---|
| 1 | 4.8 | 7 | 0.9 |
| 2 | 4.8 | 8 | 4.7 |
| 3 | 11.1 | 9 | 8.2 |
| 4 | 18.0 | 10 | 30.5 |
| 5 | 5.7 | 11 | 15.5 |
| 6 | 3.8 | 12 | 0.5 |

Table 2 shows the yields of the hexane, ethyl acetate, and methanol extracts from 2.0 kg of lyophilized roots and the yield of the compounds in each of the extracts.

TABLE 2

Yield of compounds in extracts from 2.0 kg of lyophilized roots

| | Yield | | | |
|---|---|---|---|---|
| Compound | hexane extract (25 g) | ethyl acetate extract (23 g) | methanol extract (130 g) | Combined Yield |
| 1 + 2 | 19 mg | — | — | 19 mg |
| 3 | — | 15.4 mg | 16.7 mg | 22.1 mg |
| 8 | — | 9.3 mg | — | 9.3 mg |

TABLE 2-continued

Yield of compounds in extracts from 2.0 kg of lyophilized roots

| | Yield | | | |
|---|---|---|---|---|
| Compound | hexane extract (25 g) | ethyl acetate extract (23 g) | methanol extract (130 g) | Combined Yield |
| 4 | — | 1.0 mg | 34.9 mg | 35.9 mg |
| 5 | — | — | 11.4 mg | 11.4 mg |
| 6 | — | 3.4 mg | 4.1 mg | 7.5 mg |
| 1a + 2a | NA | NA | NA | NA |
| 9 | — | — | 16.3 mg | 16.3 mg |
| 10 | — | — | 31 mg | 31 mg |
| 11 | — | — | 61 mg | 61 mg |
| 7 | — | — | 1.8 mg | 1.8 mg |

EXAMPLE 2

The physical characteristics of compounds 1 and 2 were determined to be as follows.

$^1$H NMR spectra were recorded at 500 and 600 MHz on Varian VRX (500 MHz) and Varian INOVA (600 MHz) instruments (Palo Alto, Calif.), respectively. 13C NMR spectra were obtained at 125 MHz on a Varian VRX instrument. NMR spectra of compounds 1 and 2 were obtained in $CDCl_3$. Standard pulse sequences were employed for all 1D ($^1$H, $^{13}$C, DEPT, selective $^1$H decoupling, and difference NOE) and 2D (DQF-COSY, long-range COSY, NOESY, HMQC, and HMBC) NMR experiments. Mass spectra were acquired at the Michigan State University Mass Spectrometry Facility using a JOEL AX-505H double-focusing mass spectrometer operating at 70 eV for EIMS analysis and a JOEL HX-110 double-focusing mass-spectrometer (Peabody, Mass.) operating in the positive ion mode for FABMS experiments. The UV spectra were recorded in EtOH using a Shimadzu UV-260 recording spectrophotometer (Kyoto, Japan). IR spectra were obtained on a Mattson Galaxy Series FTIR 3000 using WinFIRST software (Thermo Nicolet, Madison, Wis.). Optical rotations were measured with a Perkin-Elmer Polarimeter 341 (Shelton, Conn.). Melting points were determined using a Thomas Model 40 Hot Stage (Philadelphia, Pa.).

The hexane extract was subjected to a series of chromatographic procedures leading to the isolation of 12 mg of fine yellow needles following crystallization from $CHCl_3$-hexane. Initial inspection of the $^1$H and $^{13}$C NMR spectra of this product indicated a doubling of most proton and carbon signals that suggested it was perhaps a large dimeric compound composed of more than 31 unique carbon nuclei. However, positive FABMS indicated a major signal at m/z 295 [M+H]$^+$ that suggested the product was a mixture of two structurally related isomers each with a formula of $C_{18}H_{14}O_4$. This was supported by the presence a significant fragment ion at m/z 273 [M+H–$H_2$O]$^+$. Further evidence was also provided by HMBC experiment that showed two sets of contours representing the $^{2-3}J_{CH}$ connectivities for two compounds each composed of 18 carbon and 14 proton spins. Extensive efforts to separate these two compounds employing Si gel MPLC and TLC, ODS MPLC and preparative HPLC, and crystallization using a variety of solvent systems proved unsuccessful. Further attempts were made to separate the acetylated products (1a and 2a) from one another, but this method also failed. Therefore, the structure elucidation and full $^1$H and $^{13}$C NMR assignments of compounds 1 and 2 were performed on the inseparable 1:1 mixture of these two constitutional isomers.

Compounds 1 and 2 were determined to each be composed of substituted 1-hydroxyanthraquinone moieties. Evidence for this came from a combination of HRFABMS with m/z 295.0971 [M+H]$^+$ (calculated 295.0970) and spectroscopic studies. The IR spectrum of compound 1 and 2 exhibited a number of diagnostic absorption bands at 3438 (broad, O—H stretch), 1670 (C=O stretch, non-chelated), and 1633 cm$^{-1}$ (C=O stretch, chelated). The UV spectrum showed $\lambda_{max}$=403 nm suggesting the presence of a single peri-hydroxyl functionality (Schripsema et al., Phytochem. 51: 55–60 (1999)). This was supported by the $^1$H NMR spectrum that revealed two sharp singlets at $\delta_H$ 12.90 and 12.95 that were both eliminated upon D$_2$O exchange. Further evidence for the presence of a single hydroxyl functionality in compounds 1 and 2 came from their acetylation products 1a and 2a that both exhibited the same molecular ion at m/z 337.1068 [M+H]$^+$ (calculated for C$_{20}$H$_{17}$O$_5$, 337.1076) representing the addition of an acetyl moiety. The $^1$H NMR spectrum of 1a and 2a no longer displayed any down field peaks between $\delta_H$ 12 and 13 while the $^{13}$C NMR spectrum exhibited new signals at $\delta_C$ 19.6 (—COCH$_3$) and 169.0 (—COCH$_3$).

$^1$H NMR and DEPT experiments revealed the presence of two aromatic ($\delta_C$ 20.2 q×2, 21.9 q, and 22.0 q) and one acetyl ($\delta_C$ 31.9 q×2) methyl groups in both compounds 1 and 2. Data from the HMBC experiment (Table 3) provided evidence for the assignment of these functionalities as shown for compounds 1 and 2. Further support in favor of this conclusion was obtained from long-range COSY and difference NOE experiments FIGS. 2A and 2B. Both compounds 1 and 2 exhibited reciprocal NOE correlations upon irradiation of the methyl protons of C-12 (both $\delta_H$ 2.59) and 1-OH's ($\delta_H$ 12.95 and 12.90, respectively). In addition, NOE enhancements and long-range COSY correlations were noted between the methyl protons of C-13 (both $\delta_H$ 2.37) and the H-4 aromatic singlet (both $\delta_H$ 7.61). Together, these data confirmed the proposed ring B assignments for compounds 1 and 2.

Figure 2A:
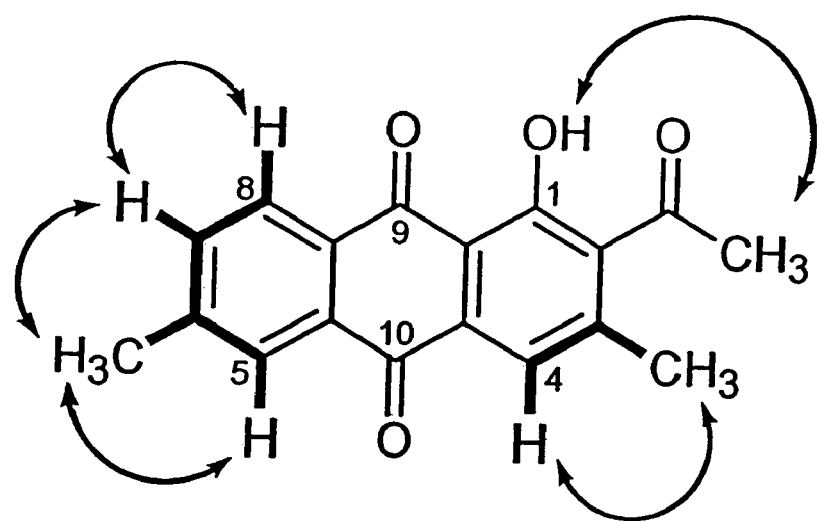
FIG. 2A shows the difference NOE (→) and long-range COSY (—) correlations used to establish the structure of compound 1 (kwanzoquinone A).
Figure 2B:
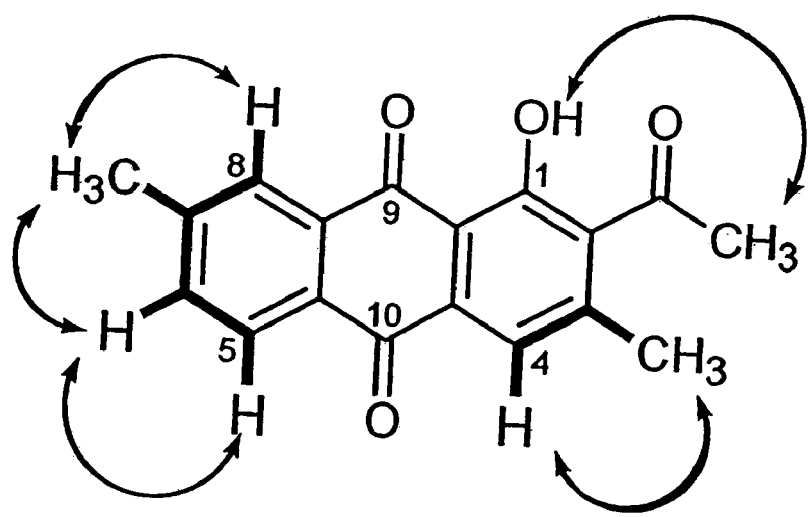
FIG. 2B shows the difference NOE (→) and long-range COSY (—) correlations used to establish the structure of compound 2 (kwanzoquinone B).

Compound 1 exhibited reciprocal NOE enhancements and COSY correlations amongst H-7 ($\delta_H$ 7.58 d, J=7.5 Hz) and H-8 ($\delta_H$ 8.15 d, J=7.5 Hz), as well as, between the methyl protons of C-14 ($\delta_H$ 2.51 s) and protons at positions H-7 and H-5 ($\delta_H$ 8.04 s) (FIG. 2A). These evidence confirmed that the aromatic methyl C-14 ($\delta_H$ 21.9) was attached at position 6 on ring A of compound 1. Compound 2 differed by displaying reciprocal NOE enhancements and long-range COSY correlations between the methyl protons of C-14 ($\delta_H$ 2.51 s) and protons H-6 ($\delta_H$ 7.58 d, J=7.5 Hz) and H-8 ($\delta_H$ 8.05 s) (FIG. 2B). Similar NOE and COSY correlations were noted between H-6 and H-5 ($\delta_H$ 8.13 d, J=7.5 Hz). Therefore, the assignment of the aromatic methyl C-14 ($\delta_C$ 22.0) was confirmed at position 7 on ring A of compound 2. Both compounds 1 and 2 are newly discovered compounds which have been given the name kwanzoquinones A and B, respectively in honor of their biogenic source.

Kwanzoquinones A and B (compounds 1 and 2): yellow needles; melting point 165–167° C.; UV $\lambda_{max}$ (EtOH) 212, 262, 287, 403 nm; IR (KBr) $\nu_{max}$ 3438, 1700, 1696, 1691, 1685, 1670, 1652, 1630, 1595, 1559 cm$^{-1}$; $^1$H NMR $^{13}$C NMR data, see Table 3; HRFABMS m/z 295.0971 [M+H]$^+$ (calculated for C$_{18}$H$_{15}$O$_4$, 295.0970).

TABLE 3

NMR Spectra Data for Kwanzoquinones A (1) and B (2) in CDCL$_3$[a]

| | 1 | | | 2 | | |
|---|---|---|---|---|---|---|
| position | $\delta_h$(J in Hz)[b] | $\delta_c$[c] | HMBC[d] | $\delta_h$(J in Hz)[b] | $\delta_c$[c] | HMBC[d] |
| 1 | | 159.6(s) | 1-OH | | 159.6(s) | 1-OH |
| 2 | | 114.4[e](S) | 1-OH, H-13, H-4 | | 114.5[e](s) | 1-OH, H-13, H-4 |
| 3 | | 144.7[f](s) | H-4, H-13 | | 144.9[f](s) | H-4, H-13 |
| 4 | 7.61(s) | 121.5(d) | H-13 | 7.61(s) | 121.5(d) | H-13 |
| 4a | | 133.1(s) | H-4 | | 133.19(s) | H-4 |
| 5 | 8.04(s) | 127.8(d) | H-14 | 8.13(d, 7.5) | 127.7(d) | H-6 |
| 6 | | 146.2(s) | H-8, H-14 | 7.58(d, 7.5) | 135.6(d) | H-8, H-14 |
| 7 | 7.58(d, 7.5) | 135.1(d) | H-5, H-14 | | 145.6(s) | H-5, H-14 |
| 8 | 8.15(d, 7.5) | 127.1(d) | H-7 | 8.05(s) | 127.2(d) | H-14 |
| 8a | | 133.4(s) | H-8 | | 131.2(s) | H-8 |
| 9 | | 188.1(s) | H-8 | | 188.5(s) | H-8 |
| 9a | | 135.7[g](s) | 1-OH, H-4 | | 135.8[g](s) | 1-OH, H-4 |
| 10 | | 182.3(s) | H-4, H-5 | | 181.9(s) | H-4, H-5 |
| 10a | | 130.9(s) | H-5 | | 133.0(s) | H-5 |
| 11 | | 203.0(s) | H-12 | | 203.0(s) | H-12 |
| 12 | 2.59(s) | 31.9(q) | | 2.59(s) | 31.9(q) | |
| 13 | 2.37(s) | 20.2(q) | H-4 | 2.37(s) | 20.2(q) | H-4 |
| 14 | 2.51(s) | 21.9[h](q) | H-5, H-7 | 2.51(s) | 22.0[h](q) | H-6, H-8 |
| 1-OH | 12.95(s) | | | 12.90(s) | | |

[a]All spectra were recorded using 12 mg of a 1:1 mixture of compounds 1 and 2 dissolved in 1 mL of CDCl$_3$ with a 5 mm probe at 25° C.
[b]Recorded at 500 MHz.
[c]Recorded at 125 MHz. Multiplicities were determined by DEPT experiment.
[d]HMBC data were recorded using a
$^n$J$_{CH}$ = 8 Hz and are expressed as protons exhibiting
$^{2-3}$J$_{CH}$ couplings to the carbons as indicated.
[e-h]Assignments may be interchanged.

EXAMPLE 3

The physical characteristics for compound 3 were determined as in Example 2 except that all NMR spectra were recorded in DMSO-$d_6$ (Cambridge Isotope Laboratories, Inc., Andover, Mass.). The characteristics are as follows.

The MeOH extract was subjected to repeated ODS and SEPHADEX LH-20 gel column chromatography yielding compounds 3–12. Following purification, compound 3 was obtained from MeOH as orange needles. HREIMS (m/z 270.0532 [M]$^+$ (calculated for $C_{15}H_{10}O_5$, 270.0528)) and spectral evidence (IR, UV, ID and 2D NMR) confirmed that compound 3 (1,2,8-trihydroxy 3-methylanthraquinone) had been previously isolated from *Myrsine africana* L. (Myrsinaceae) and was given the trivial name 2-hydroxychrysophanol (Li and McLaughlin, J. Nat. Prod. 52: 660–662 (1989); Midiwo and Arot, Int. J. BioChemiPhysics 2: 115–116 (1993)). Previous studies had only given partial $^1$H and no $^{13}$C NMR assignments for this compound; therefore, we undertook a thorough NMR investigation of compound 3 in order to confirm its proposed structure. This is the first report of compound 3 from daylilies and the first report of its complete $^{13}$C NMR spectral date (Table 4).

2-Hydroxychrysophanol (compound 3): orange needles; melting point 239–240° C.; UV $\lambda_{max}$ (EtOH) (log ε) 208 (4.19), 235 (4.05), 258 (4.11), 426 (3.73) nm; IR (KBr) $v_{max}$ 3408, 1653, 1620, 1560, 1473, 1456, 1434, 1310, 1271, 1190, 1023 cm$^{-1}$; $^1$H NMR (DMSO-$d_6$) $\delta_H$ 12.04 (1H, brs, 1-OH), 11.90 (1H, s, 8-OH), 10.34 (1H, brs, 2-OH), 7.76 (1H, dd, 8.0, 7.5, H-6), 7.66 (1H, dd, 7.5, 1.0, H-5), 7.55 (1H, s, H-4), 7.31 (1H, dd, 8.0, 1.0, H-7), 2.26 (1H, s, 3-CH$_3$; $^{13}$C NMR, see Table 4; EIMS m/z 270 [M]$^+$ (100), 253(2), 242(8), 213(4), 196(3), 185(2), 168(5), 139(11); HREIMS m/z 270.0532[M]$^+$ (calculated for $C_{15}H_{10}O_5$, 270.0528) (for literature values refer to Li and McLaughlin, ibid.; Midiwo and Arot, ibid.).

TABLE 4

$^{13}$C NMR Assignments for Compounds 3 to 7 and 9[a]

| position | 3 | 4 | 5 | 6 | 7 | 9 |
|---|---|---|---|---|---|---|
| 1 | 194.4s | 153.9s | 153.9s | 149.1s | 153.4s | 158.6s |
| 2 | 150.2s | 147.7s | 147.7s | 148.4s | 146.0s | 131.2s |
| 3 | 132.3s | 141.4s | 141.5s | 136.7s | 145.3s | 140.4s |
| 4 | 122.8d | 121.5d | 121.4d | 119.0d | 117.9d | 112.0d |
| 4a | 123.1s | 128.02 | 128.0s | 123.3s | 128.2s | 136.2s |
| 5 | 119.0d | 119.0d | 119.0d | 119.1d | 119.1d | 118.1d |
| 6 | 137.3d | 137.1d | 137.1d | 137.4d | 137.2d | 135.9d |
| 7 | 123.7d | 124.1d | 124.0d | 123.7d | 124.0d | 124.2d |
| 8 | 161.2s | 161.2s | 161.2s | 161.3s | 161.2s | 161.3s |
| 8a | 115.9s | 115.9s | 115.9s | 116.0s | 116.1s | 116.7s |
| 9 | 192.2s | 191.5s | 191.4s | 192.3s | 191.7s | 189.2s |
| 9a | 114.3s | 115.2s | 115.2s | 114.6s | 115.7s | 122.4s |
| 10 | 180.1s | 180.8s | 180.6s | 180.2s | 180.8s | 181.8s |
| 10a | 133.7s | 133.2s | 133.1s | 133.8s | 133.3s | 132.3s |
| 11 | 16.4q | 17.2q | 17.2q | 57.8t | 58.1t | 19.5q |
| 12 | | | | | | 167.8s |
| 1' | | 102.9d | 102.8d | | 102.7d | |
| 2' | | 74.2d | 74.0d | | 74.1d | |
| 3' | | 76.3d | 76.0d | | 76.2d | |
| 4' | | 69.7d | 69.7d | | 69.7d | |
| 5' | | 77.3d | 73.8d | | 77.2d | |
| 6' | | 60.8t | 63.7t | | 60.7t | |
| 1" | | | 166.4s | | | |
| 2" | | | 41.1t | | | |
| 3" | | | 167.4s | | | |

[a]Data recorded in DMSO-$d_6$ at 125 MHz at 25° C. Multiplicities were determined by DEPT experiment and confirmed by analysis of HMQC spectra.

EXAMPLE 4

The physical characteristics for compound 4 were determined as in Example 3. The characteristics are as follows.

The MeOH extract was subjected to repeated ODS and SEPHADEX LH-20 gel column chromatography yielding compounds 4. Compound 4 was obtained as yellow needles and exhibited many spectral characteristics similar to 3. The IR spectrum of 4 revealed absorption bands at 3455 (broad, O—H stretch), 1671 (C=O stretch, non-chelated), and 1624 cm$^{-1}$, (C=O stretch, chelated). The UV spectrum presented a $\lambda_{max}$=429 nm that was in accord with the presence of two peri-hydroxyl functionalities (Schripsema ibid.; Brauers et al., J. Nat. prod. 63: 739–745 (2000); Li et al., J. Nat. Prod. 63: 653–656 (2000)). In addition, the $^1$H NMR spectrum showed two down field peaks ($\delta_H$ 12.00 s and 12.04 brs) that were exchangeable with $D_2O$. Together this evidence supported the presence of a 1,8-dihydroxyanthraquinone chromaphore for compound 4.

FABMS gave m/z 433 [M+H]$^+$ that represented a molecular composition of $C_{21}H_{21}O_{10}$. $^1$H NMR provided important evidence for the substitution pattern of rings B and A in compound 4. Three protons representing an ABC spin system at $\delta_H$ 7.70 (dd, J=1.0, 7.5 Hz), 7.79 (dd, J=7.5, 8.0 Hz), and 7.36 (dd, J=1.0, 8.0 Hz) were identified as occupy contiguous positions attached to C-5, C-6, and C-7, respectively on ring A of compound 4. $^{13}$C NMR and DEPT experiments (Table 4) provided further evidence for the identity of the substituents attached to ring B of compound 4 with one methine ($\delta_C$ 121.5), one C-linked ($\delta_C$ 141.4) methyl ($\delta_C$ 17.2), and two quaternary carbon ($\delta_C$ 147.7 and 153.9) linked with a hetero-atom. These carbons were assigned positions in ring B of compound 4 based on their respective chemical shifts and the results from HMBC and HMQC experiments. Five additional methine ($\delta_C$ 69.7, 74.2, 76.3, 77.3, and 102.9) and one methylene ($\delta_C$ 60.8) spins were observed that exhibited chemical shift values that coincided with those for a glucopyranose moiety. The glucopyranose was assigned a β-configuration based on the coupling of H-1' ($\delta_H$ 5.07, d, J=7.5 Hz). The complete structure of compound 4 was confirmed based on HMBC experiment. Compound 4 is a newly discovered anthraquinone glycoside which has been given the name kwanzoquinone C.

Kwanzoquinone C (compound 4): fine yellow needles; melting point 233–234° C.; [α]$^{20}_D$-46° (c 0.031, EtOH); UV $\lambda_{max}$ (EtOH) (logε) 206(4.20), 227(4.23), 260(4.17), 429 (3.78) nm; IR (KBr) $v_{max}$ 3422, 1671, 1624, 1559, 1473, 1382, 1373, 1293, 1263, 1067 cm$^{-1}$; $^1$H NMR (DMSO-$d_6$) $\delta_H$ 12.04 (1H, brs, 8-OH), 12.00 (1H, s, 1-OH), 7.79 (1H, dd, J=7.5, 8.0 Hz, H-6), 7.70 (1H, dd, J=1.0, 7.5 Hz, H-5), 7.61 (1H, s, H-4), 7.36 (1H, dd, J=1.0, 8.0 Hz), 5.07 (1H, d, J=7.5 Hz, H-1'), 3.60 (1H, ddd, J=2.0, 5.5, 12.0 Hz, H-6a'), 342 (1H, ddd, J=6.0, 11.5, 11.5 Hz, H-6b'), 3.31 (1H, m, H-2'), 2.35 (1H, m, H-3'), 3.16 (1H, m, H-4'), 3.13 (1H, m, H-5'), 2.42 (3H, s, H-11); $^{13}$C NMR data, see Table 4; HRFABMS m/z 433.1139 [M+H]$^+$ (calculated for $C_{21}H_{21}O_{10}$, 433.1135).

EXAMPLE 5

The physical characteristics for compound 5 were determined as in Example 3. The characteristics are as follows.

Figure 3:
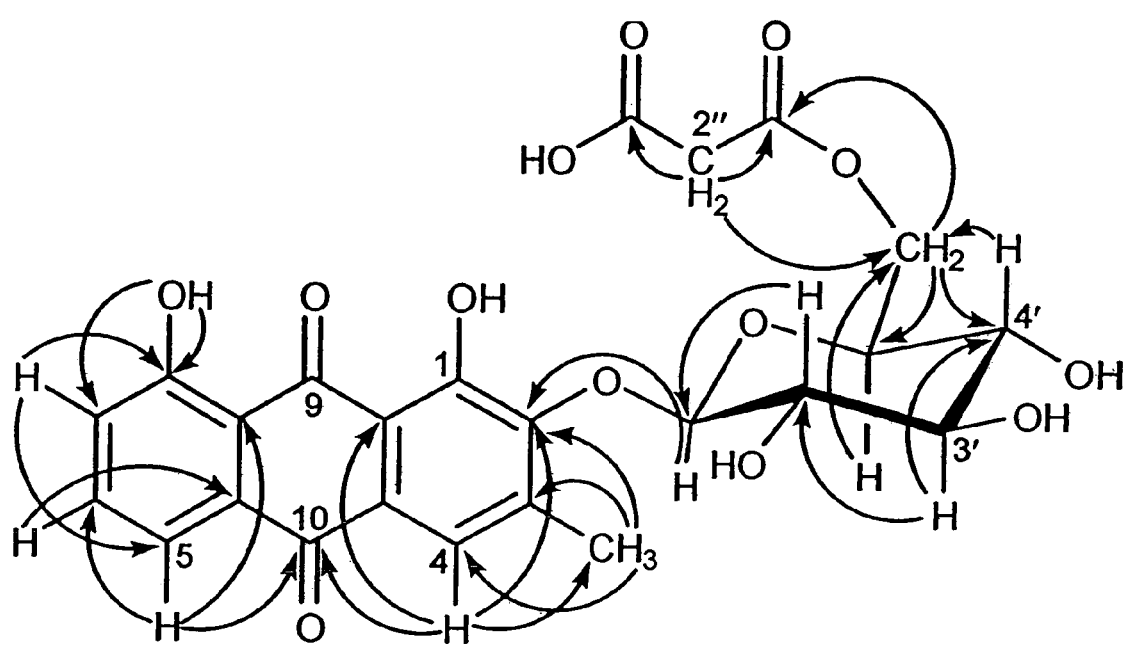
FIG. 3 shows selected HMBC correlations used to determine the structure of compound 5 (kwanzoquinone D).

The MeOH extract was subjected to repeated ODS and SEPHADEX LH-20 gel column chromatography yielding compounds 5. The molecular formula of compound 5 was determined to be $C_{24}H_{22}O_{13}$ based on FABMS analysis that exhibited m/z 519 [M+H]$^+$. The spectral data of compound 5 were very similar to those obtained for compound 4. The most significant difference was observed in the $^1$H and $^{13}$C NMR spectra (Table 4) with the addition of three new carbon signals at $\delta_C$ 41.1, 166.4, and 167.4 and a new proton resonance at $\delta_H$ 3.23 integrating for two hydrogens. These chemical shifts were characteristic of those expected for a malonyl moiety. The linkage of the malonyl group in compound 5 was established as malonyl-(1→6)-β-D-glucopyranoside based on the observed down field shift of C-6' to $\delta_C$ 63.7 verses that observed for compound 4 (Δ=+2.9 ppm). These observations were verified by HMBC analyses (FIG. 3) which exhibited weak $^4J_{CH}$ correlations from H-6a' ($\delta_H$ 4.12) and H-6b' ($\delta_H$ 4.27) to C-1" ($\delta_C$ 41.1) and H-2" ($\delta_H$ 3.23) to C-6' ($\delta_C$ 63.7). This confirmed compound 5 was a new anthraquinone malonyl-glucoside which was then named kwanzoquinone D.

Kwanzoquinone D (compound 5): golden-yellow needles; melting point 174–175° C.; [α]$^{20}_D$-313° (c 0.008, EtOH); UV λ$_{max}$ (EtOH) (logε) 205(4.28), 227(4.35, 260(4.31), 290 sh (3.91), 430(3.96) nm; IR (KBr) ν$_{max}$ 3430, 1434, 1717, 1699, 1670, 1653, 1559, 1457, 1268, 1066 cm$^{-1}$; $^1$H NMR (DMSO-d$_6$) $\delta_H$ 12.57 (1H, brs, 1-OH), 11.96 (1H, s, 8-OH), 7.77 (1H, dd, J=7.5, 8.0 Hz, H-6), 7.67 (1H, dd, J=1.0, 7.5 Hz, H-5), 7.57 (1H, s, H-4), 7.33 (1H, dd, J=1.0, 8.0 Hz), 5.06 (1H, d, J=7.5 Hz, H-1'), 4.27 (1H, dd, J=2.5, 11.9 Hz, H-6a'), 4.12 (1H, dd, J=6.5, 11.9 Hz, H-6b'), 3.38 (1H, m, H-5'), 3.33 (1H, m, H-2'), 3.28 (1H, m, H-3'), 3.23 (2H, s, H-2"), 3.21 (1H, m, H4'), 2.37 (3H, s, H-11); $^{13}$C NMR data, see Table 4; HRFABMS m/z 519.1139 [M+H]$^+$ (calculated for C$_{24}$H$_{23}$O$_{13}$, 59.1151).

EXAMPLE 6

The physical characteristics for compound 6 were determined as in Example 3. The characteristics are as follows.

The MeOH extract was subjected to repeated ODS and SEPHADEX LH-20 gel column chromatography yielding compound 6. EIMS analysis of compound 6 gave a molecular ion of m/z 286 [M]$^+$ indicating a molecular formula of C$_{15}$H$_{10}$O$_6$. The UV (λ=426 nm) and IR (absorption bands at 3469 (broad, O—H stretch), 1667 (C=O stretch, non-chelated), and 1620 cm$^{-1}$ (C=O stretch, chelated)) spectra suggested a 1,8-dihydroxyanthraquinone chromaphore for compound 6. The $^1$H NMR spectrum provided evidence for four exchangeable protons at δ 12.06, 11.92, 10.47, and 5.40 representing three aromatic and one aliphatic hydroxyl functionalities. An ABC spin system was observed with protons at $\delta_H$ 7.70 (dd, J=0.5,7.8 Hz), 7.78 (overlapping dd, J=7.8, 7.8 Hz), and 7.33 (dd, J=0.5, 7.8 Hz) occupy contiguous positions attached to C-5, C-6, and C-7, respectively on ring A of compound 6.

Figure 4:
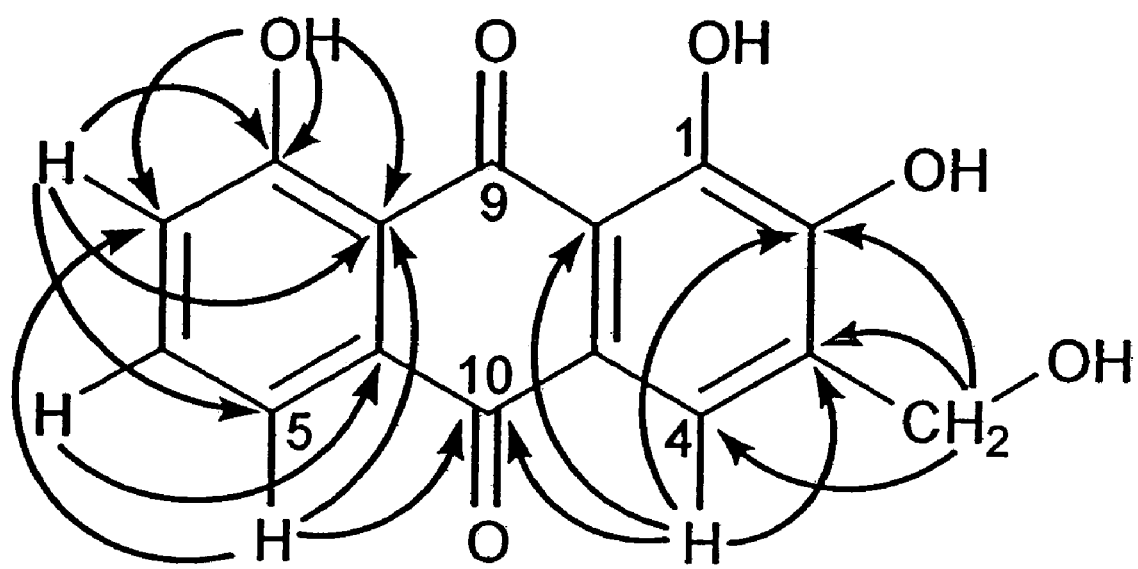
FIG. 4 shows selected HMBC correlations used to determine the structure of compound 6 (kwanzoquinone E).

$^1$H and $^{13}$C NMR and DEPT experiments of compound 6 (Table 4) gave evidence that ring A possessed quaternary carbons with ortho-hydroxyl functionalities (δ 149.1 s and 148.4 s), a hydroxy-methylene moiety $\delta_H$ 4.59 s, 2H and $\delta_C$ 57.8 t) attached to a quaternary carbon ($\delta_C$ 136.7), and a methine ($\delta_C$ 119.0). An HMBC experiment was used to make full assignments of these proton and carbon spins as shown for compound 6 (FIG. 4). Compound 6 is a newly discovered which has been named kwanzoquinone E.

Kwanzoquinone E (compound 6): fine yellow needles; melting point 196–197° C.; UV max (EtOH) (logε) 209 (4.32), 235(4.10), 258(4.27), 354(3.72), 426(3.76) nm; IR (KBr) ν$_{max}$ 3469, 1652, 1619, 1559, 1473, 1458, 1382, 1321, 1273, 1092 cm$^{-1}$; $^1$H NMR (DMSO-d$_6$) $\delta_H$ 12.06 (1H, brs, 1-OH), 11.92 (1H, s, 8-OH), 10.47 (1H, brs, 2-OH), 7.87 (1H, d, J=0.5 Hz, H-4), 7.78 (1H, dd, J=7.8, 7.8 Hz, H-6), 7.70 (1H, dd, J=0.5, 7.8 Hz, H-5), 7.33 (1H, dd, J=0.5, 7.8 Hz, H-7), 5.40 (1H, brs, 11-OH), 4.59 (2H, s, H-11); $^{13}$C NMR data, see Table 4; EIMS m/z 286 [M]$^+$ (62), 268(89), 240(56), 212(100), 184(50), 155(14), 128(19), 120(19); HREIMS m/z 286.0479 [M]$^+$ (calculated for C$_{15}$H$_{10}$O$_5$, 286.0477).

EXAMPLE 7

The physical characteristics for compound 7 were determined as in Example 3. The characteristics are as follows.

The MeOH extract was subjected to repeated ODS and SEPHADEX LH-20 gel column chromatography yielding compounds 7. Compound 7 exhibited spectral data similar to 6 with the addition of five methine ($\delta_C$ 69.7, 74.1, 76.2, 77.2, and 102.7) and one methylene ($\delta_C$ 60.7) spins that exhibited chemical shift values that coincided with those for a glucopyranose moiety. The addition of a glucopyranose moiety was confirmed by HRFABMS which gave m/z 449.1082 [M+H]$^+$ (calculated 449.1084 for C$_{21}$H$_{20}$O$_{11}$) representing a molecular formula of C$_{21}$H$_{20}$O$_{11}$ for compound 7. The glucopyranose moiety was determined to be O-linked at position 11 due to the down field shift of this carbon signal to $\delta_C$ 58.1 (Δ=+0.4) and the change in the splitting pattern of the attached protons. While the enantiotopic C-11 protons of compound 6 ($\delta_H$ 4.59, 2H) appeared as a singlet, the diastereotopic C-11 protons of compound 7 ($\delta_H$ 4.65, 1H and 4.73, 1H) were each a doublet (J=16.0 Hz) in achiral solvent (0.75 mL DMSO-d$_6$ with 2 drops D$_2$O). The assignments of all proton and carbon (Table 4) spins in compound 7 were confirmed by HMBC experiment. Compound 7 is a newly discovered conjugated anthraquinone glucoside which has been given the name kwanzoquinone F.

Kwanzoquinone F (compound 7): yellow powder; melting point 204–206° C.; [α]$^{20}_D$-38° (c 0.01, EtOH); UV λ$_{max}$ (EtOH) (logε) 228(4.04), 259(4.03), 291(3.57), 432(3.68) nm; IR (KBr) ν$_{max}$ 3450, 1698, 1684, 1652, 1635, 1559, 1540, 1457, 1262, 1027 cm$^{-1}$; $^1$H NMR (0.75 mL DMSO-d$_6$/2 drops D$_2$O) $\delta_H$ 7.88 (1H, s, H-4), 7.79 (1H, dd, J=7.5, 8.0 Hz, H-6), 7.71 (1H, dd, J=1.0, 7.5 Hz, H-5), 7.36 (1H, dd, J=1.0, 8.0 Hz, H-7), 5.07 (1H, d, J=7.5 Hz, H-1'), 4.37 (1H, d, J=16.0 Hz, H-11a), 4.65 (1H, d, J=16.0 Hz, H-11b), 3.60 (1H, d, J=3.0, 12.5 Hz, H-6a'), 3.40 (1H, dd, J=5.5, 12.0 Hz, H6-b'), 3.26 (1H, m, H-2'), 3.25 (1H, m, H-3'), 3.15 (1H, m, H-4'), 3.12 (1H, m, H-5'); C NMR data, see Table 4; HRFABMS m/z 433.1132 [M+H]$^+$ (calculated for C$_{21}$H$_{21}$O$_{10}$, 433.1135).

EXAMPLE 8

The MeOH extract was subjected to repeated ODS and SEPHADEX LH-20 gel column chromatography yielding compounds 8. Compound 8 was obtained as an amorphous yellow powder and its spectral data were found to match those reported for the known anthraquinone rhein (Danielsen and Aksnes, Magn. Reson. Chem. 30: 359–360 (1992)).

EXAMPLE 9

The physical characteristics for compound 9 were determined as in Example 3. The characteristics are as follows.

The MeOH extract was subjected to repeated ODS and SEPHADEX LH-20 gel column chromatography yielding compounds 9. Compound 9 exhibited spectral data that were similar to compound 8 with the main differences in the $^1$H NMR spectrum being the loss of an aromatic doublet (ca $\delta_H$ 8.15, 1H, J=1.5 Hz) and the concomitant loss of splitting in the proton signal at $\delta_H$ 7.59 (s, 1H) indicating that position 2 in ring B of compound 9 was substituted. These observations coincided with the appearance of an aromatic methyl ($\delta_H$ 2.67 s, 3H and $\delta_C$ 19.5 q) and the down field shift of C-2 in compound 8 from $\delta_C$ 124.2 to 131.2 (Δ=+7.0 ppm) in compound 9 (Table 4). HMBC experiment was able to confirm that this methyl was a substituent of C-2 based on the long-range coupling of the C-11 methyl protons to C-2 ($\delta_C$ 131.2) and C-3 ($\delta_C$ 140.4). Compound 9 is a newly discovered anthraquinone which has been named kwanzoquinone G.

Kwanzoquinone G (compound 9): yellow powder; melting point 235–236° C.; UV $\lambda_{max}$ (EtOH) (logε) 219(4.25), 283(4.19), 413(3.63) nm; IR (KBr) $v_{max}$ 3420, 1717, 1700, 1670, 1634, 1577, 1365, 1320, 1261, 1223 cm$^{-1}$; $^1$H NMR (DMSO-d$_6$) $\delta_H$ 12.82 (1H, s, 8-OH), 12.81 (2H, brs, 1-OH and 12-OH), 7.67 (1H, dd, J=8.1, 8.1 Hz, H-6), 7.57 (1H, dd, J=1.2, 8.1 Hz, H-5), 7.56 (1H, s, H-4), 7.28 (1H, dd, J=1.5, 8.1 Hz, H-7), 2.67 (3H, s, H-11); $^{13}$C NMR data, see Table 4; HRFABMS m/z [299.0547 M+H]$^+$ (calculated for C$_{16}$H$_{11}$O$_6$, 299.0556).

EXAMPLE 10

The physical characteristics for compound 10 were determined as in Example 3. The characteristics are as follows.

The MeOH extract was subjected to repeated ODS and SEPHADEX LH-20 gel column chromatography yielding compounds 3–12. FABMS of compound 10 provided a molecular ion of m/z 525 [M+H]$^+$ and the $^{13}$C NMR spectrum exhibited ten sp$^2$ carbon signals between 110 and 155 ppm along with 12 additional sp$^3$ carbon signals that were characteristic of a rutinose moiety. In light of the presence of three additional carbon signals that represented an aromatic methyl ($\delta_C$ 19.0) and an acetyl moiety ($\delta_C$ 31.9 and 204.4), it was determined that compound 10 was a substituted naphthalene diglycoside. HMQC and HMBC experiments established the aglycone portion of compound 10 as 2-acetyl-3-methyl-1,8-dihydroxynaphthalene, dianellidin. Further scrutiny of the HMBC data provided for the assignment of an 8-O-linkage to the rutinoside moiety based on a correlation from H-1' ($\delta_H$ 5.04, d, J=7.5 Hz) to C-8 ($\delta_C$ 154.2 s). According to these data, compound 10 was identified as dianellin, previously isolated from *Dianella* spp. (Liliaceæ) (Batterham et al., Aust. J. Chem. 14: 637–642 (1961)). This is the first report showing compound 10 is present in daylilies and the first report detailing its $^1$H and $^{13}$C NMR spectral data.

Dianellin (compound 10): white needles; melting point 156–157° C.; [α]$^{20}_D$-137° (c 0.01, EtOH); UV $\lambda_{max}$ (EtOH) (logε) 225(4.75), 301(3.80), 334(3.78) nm; IR (KBr) $v_{max}$ 3416, 2923, 1651, 1633, 1579, 1467, 1443, 1356, 1270, 1067 cm$^{-1}$; $^1$H NMR (DMSO-d$_6$) $\delta_H$ 9.53 (1H, brs, 1-OH), 7.47 (1H, dd, J=1.0, 8.0 Hz, H-5, 7.40 (1H, dd, J=8.0, 8.0 Hz, H-6), 7.30 (1H, dd, J=1.0, 8.0 Hz, H-7), 7.21 (1H, s, H-4, 5.04 (1H, d, J=7.5 Hz, H-1'), 4.62 (1H, d, J=1.5 Hz, H-1"), 3.93 (1H, dd, J=1.5, 11.0 Hz, H-6a'), 3.68 (1H, m, H-2"), 3.59 (1H, m, H-5'), 3.50 (2H, m, H-4'), 3.18 (1H, m, H-4'), 2.52 (3H, s, H-12), 2.25 (3H, s, H-13), 1.12 (3H, d, J=6 Hz, H-6'); $^{13}$C NMR (DMSO-d$_6$) $\delta_C$ 204.4 (s, C-11), 154.2 (s, C-8), 150.2 (s, C-1), 135.7 (s, C-10), 132.8 (s, C-3), 1.27.3 (s, C-6), 125.2 (s, C-2), 122.3 (d, C-5), 119.4 (d, C-4), 113.2 (s, C-9), 110.7 (d, C-7), 102.6 (d, C-1'), 100.7 (d, C-1"), 76.2 (d, C-3'), 76.0 (d, C-5'), 73.3 (d, C-2'), 71.9 (d, C-4"), 70.7 (d, C-3"), 70.4 (d, C-2"), 70.1 (d, C-4'), 68.4 (d, C-5"), 66.6 (t, C-6'), 31.9 (q, C-12), 19.0 (q, C-13), 17.7 (q, C-6"); HRFABMS m/z 525.1970 [M+H]$^+$ (calculated for C$_{25}$H$_{33}$O$_{12}$, 525.1972).

EXAMPLE 11

The physical characteristics for compound 11 were determined as in Example 3. The characteristics are as follows.

Figure 5:
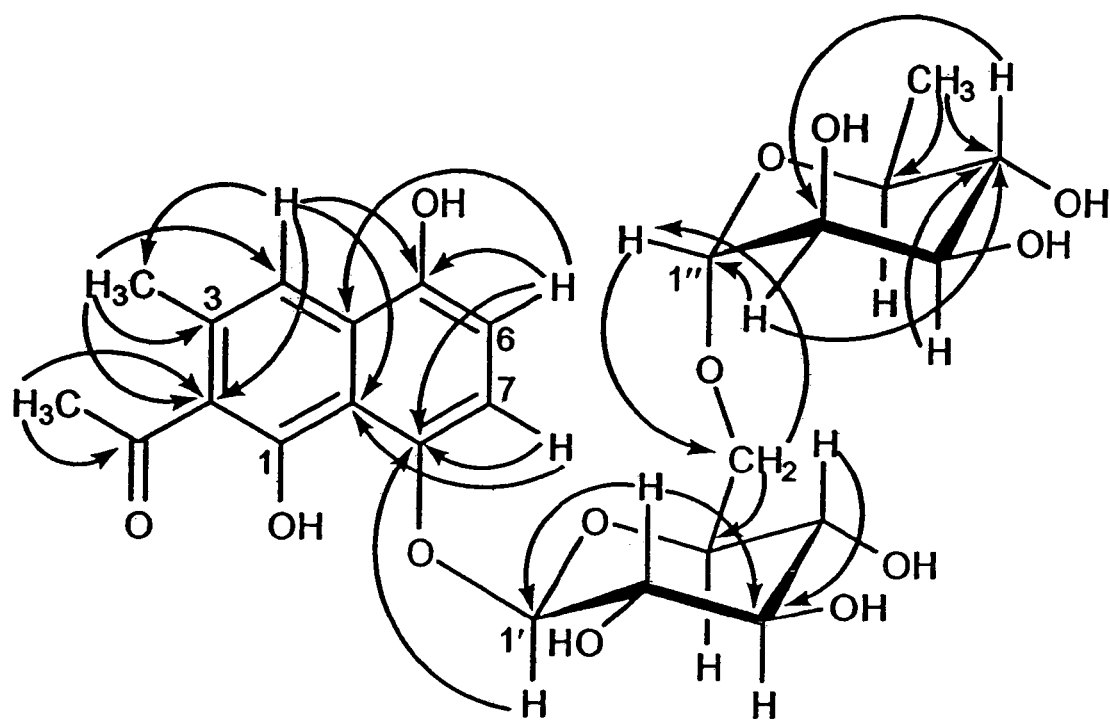
FIG. 5 shows selected HMBC correlations used to determine the structure of compound 11 (5-hydroxydianellin).

The MeOH extract was subjected to repeated ODS and SEPHADEX LH-20 gel column chromatography yielding compounds 11. The $^1$H and $^{13}$C NMR and DEPT data of compound 11 were very similar to those observed for compound 10 with the loss of one aromatic methine spin that was replaced by a quaternary carbon ($\delta_C$ 148.3) that was linked to a hetero-atom. FABMS analysis yielded a molecular ion of m/z 541 [M+H]$^+$ which accounted for the addition of an oxygen atom giving a molecular formula of C$_{25}$H$_{32}$O$_{13}$. A comparison of the $^1$H and $^{13}$C NMR data for the aglycone portion of compound 11 with that previously reported for the naphthalene glycoside stelladerol, demonstrated that both possessed the same aglycon moiety. These compounds differed, however, with respect to their glycoside portion. HMBC correlation data for compound 11 (FIG. 5) showed that it possessed an 8-O-β-D-rhamnopyranosyl -(1→6)-β-D-glucopyranoside moiety. Significant HMBC correlations that were used to deduce these connectivities included those observed for H-1' ($\delta_H$ 4.87, d, J=7.5 Hz) to C-8 ($\delta_C$ 146.7 s), and H-6a' ($\delta_H$ 3.92 m) and H-6b' ($\delta_H$ 3.52 m) to C-1" ($\delta_C$ 100.7 d), as well as, from H-1" ($\delta_H$ 4.61 m) to c-6' ($\delta_C$ 66.6 t). Based on these data, compound 11, 5-hydroxydianellin (1-(1,5,8-trihydroxy-3-methyl-napthalen-2-yl)-ethanone-8-O-β-D-rhamnopyranosyl-(1→6)-β-D-glucopyranoside), was identified as a newly discovered naphthalene glycoside.

5-Hydroxydianellin (compound 11): yellow amorphous solid; melting point 152–153° C.; [α]$^{20}_D$-212° (c 0.01, EtOH); UV $\lambda_{max}$ (EtOH) (log ε) 224(4.92), 318(4.13), 346 (4.15) nm; IR (KBr) $v_{max}$ 3420, 1698, 1684, 1653, 1635, 1559, 1457, 1364, 1257, 1059 cm$^{-1}$; $^1$H NMR (DMSO-d$_6$) $\delta_H$ 9.71 (2H, brs, 1-OH and 5-OH), 7.43 (1H, s, H-4), 7.16 (1H, d, J=8.0, H-7), 6.76 (1H, d, J=8.0, H-6), 4.87 (1H, d, J=7.5, H-1'), 4.61 (1H, m, H-1"), 3.92 (1H, m, H-6a'), 3.69 (1H, brs, H-2"), 3.52 (1H, m, H-6b'), 3.51 (1H, m, H-5'), 3.50 (1H, m, H-3"), 3.48 (1H, H-5"), 3.34 (2H, m, H-2' and H-3"), 3.21 (1H, m, H-4", 3.18 (1H, m, H-4'), 2.51 (3H, s, H-12), 2.26 (3H, s, H-13), 1.14 (3H, d, J=6 Hz, H-6"); $^{13}$C NMR (DMSO-d$_6$) $\delta_C$ 204.7 (s, C-11), 150.2 (s, C-1), 148.3 (s, C-5), 146.7 (s, C-8), 131.3 (s, C-3), 126.4 (s, C-10), 125.6 (s, C-2), 114.2 (s, C-9), 113.8 (d, C-4), 111.9 (d, C-7), 108.6 (d, C-6), 103.5 (d, C-1'), 100.7 (d, C-1"), 76.3 (d, C-3'), 75.9 (d, C-5'), 73.3 (d, C-2'), 72.0 (d, C-4"), 70.8 (d, C-3"), 70.5 (d, C-2"), 70.0 (d, C-4"), 68.4 (d, C-5"), 66.6 (t, C-6'), 31.9 (q, C-12), 19.3 (q, C-13), 17.7 (q, C-6"); HRFABMS m/z 541.1910 [M+H]$^+$ (calculated for C$_{25}$H$_{33}$O$_{13}$, 541.1921).

EXAMPLE 12

The physical characteristics for compound 12 were determined as in Example 3. The characteristics are as follows.

The MeOH extract was subjected to repeated ODS and SEPHADEX LH-20 gel column chromatography yielding compounds 12. Compound 12 was obtained as a clear glass-like solid and identified as 5,7,3,4-tetrahydroxy-6-methylflavone (6-methylluteolin) that was previously reported from *Salvia nemorosa* L. (Lammiaceæ) (Milovanovic et al., J. Serb. Chem. Soc. 61: 423–429 (1996)). Its structure was confirmed based on through 1D and 2D NMR studies and by comparisons of its UV and IR spectral data with those reported in the prior art. This is the first report showing compound 12 is present in daylilies and the first report detailing its $^1$H and $^{13}$C NMR spectral data.

6-Methyllueolin (compound 12): yellow glass-like solid; UV and IR data were identical to values in Milovanovic et al. (ibid.); $^1$H NMR (DMSO-$d_6$) $\delta_H$ 10.92 (1H, s, 5-OH), 9.71 (1H, s, 7-OH), 9.55 (1H, s, 4'-OH), 9.23 (1H, s, 3'-OH), 7.40 (1H, d, J=2.0 Hz, H-2'), 7.16 (1H, dd, J=2.0, 8.5 Hz, H-6'), 6.80 (1H, d, J=8.5 Hz, H-5'), 6.47 (1H, s, H-3), 6.32 (1H, s, H-8), 1.92 (3H, s, —CH$_3$); $^{13}$C NMR (DMSO-$d_6$) $\delta_C$ 180.1 (s, C-4), 165.0 (s, C-5), 164.2 (s, C-9), 154.5 (s, C-7), 147.4 (s, C-4'), 145.6 (s, C-3'), 145.3 (s, C-2), 123.9 (d, C-6'), 123.5 (s, C-1'), 117.5 (d, C-2'), 115.8 (d, C-5'), 109.8 (d, C-3), 105.8 (s, C-6), 102.8 (s, C-10), 90.2 (d, C-8), 7.5 (q, —CH$_3$); HRFABMS m/z 301.0709 [M+H]$^+$ (calculated for $C_{16}H_{13}O_6$, 301.0712).

EXAMPLE 13

Compounds 1 to 11, including compounds 1a and 2a, were assayed for inhibitory activity against multiple life-stages (cercariae, schistosomula, and adult) of the human pathogenic trematode *Schistosoma mansoni*. Anthraquinones assayed for toxicity on *Schistosome cercariae*. The results show that compounds 3 and 6 were inhibitory. The assays were performed as follows.

*Schistosoma mansoni* (Puerto Rican strain) cercariae were collected from infected *Biomphalaria glabrata* snails by light induction as taught by Salter et al. in J. Biol. Chem. 275: 38667–38673 (2000).

One mg of each compound was separately dissolved in 100 μL DMSO. To this solution, 19.9 mL distilled water was added to make a 1:200 dilution of the solution to produce a stock solution containing 50 μg/mL of the compound.

For testing the inhibitory effect of each compound, 100 μL of stock solution containing the compound at 50 μg/mL was added to 100 μL freshly shed *S. mansoni* cercariae (approx. 50) in the wells of a 96-well assay plate to give a final volume of 200 μL wherein the concentration of the compound was 25 μg/mL. The mobility and motility of the cercariae was monitored over time.

At a concentration of 25 μg/mL, compound 3 immobilized the cercariae which sank to the bottom of the wells within 10 to 15 seconds after the addition of the solution containing compound 3. After 2, 5, 10, 15 and 30 minutes of exposure to compound 3, the solution was removed from the wells and replaced with 200 μL of fresh water. After 16 hours, 50% of cercariae which had been exposed to compound 3 for each of the exposure times were still alive and fairly active. The guts of the live cercariae were dark (a phenomenon not seen in the control wells). After 24 hours, the mortality remained at 50%. Therefore, the length of time the cercariae were exposed to compound 3 had no significant effect on survival of the cercariae. Even when compound 3 was diluted to 3.25 μg/mL, the cercariae were immobilized after 45 minutes exposure.

At a concentration of 25 μg/mL, compound 6 immobilized the cercariae which sank to the bottom of the wells within 12 to 14 minutes after the addition of the solution containing compound 6. After 2, 5, 10, 15 and 30 minutes of exposure to compound 6, the solution was removed from the wells and replaced with 200 μL of fresh water. After 16 hours, 25 to 30% of cercariae which had been treated with compound 6 for each of the exposure times were still alive but not active. The guts of the live cercariae were dark here as well. After 24 hours, all the cercariae which had been treated with compound 6 for each of the exposure times were dead (100% mortality). Therefore, the length of time the cercariae were exposed to compound 6 had no significant effect on survival of the cercariae.

None of the other compounds, including the glycosides of compounds 3 and 6 (compounds 4 and 7, respectively) exhibited any inhibitory activity against *S. mansoni*.

The results show that compound 3 is more potent at immobilizing cercariae but less toxic or lethal than compound 6 in longer-term follow-up. In light of the results, a regimen for treating a patient infected with a human pathogenic trematode would include providing a composition comprising both compound 3 to rapidly immobilize the cercariae and compound 6 to kill all the cercariae. At 0.25 ppm, compounds 3 and 6 produced essentially 100% mortality of cercariae over time as shown in FIG. 2.

Because compounds 4 and 5 can be hydrolyzed in the gut to compound 3 and compound 7 can be hydrolyzed in the gut to compound 6, a regimen for treating a patient infected with a human pathogenic trematode would include providing a composition containing compound 7 and at least one compound selected from the group consisting of compound 4 and compound 5. Further regimens would include compositions comprising compound 3 and compound 6 and compound 7 and at least one compound selected from the group consisting of compound 4 and compound 5.

EXAMPLE 14

Compounds 1–11, including 1a and 2a, were tested for activity against multiple life stages (cercariae, schistosomula, and adult) of the human pathogenic trematode *Schistosoma mansoni*.

The cercariae assays were performed as follows. *S. mansoni* (Puerto Rican strain) cercariae were obtained from infected *Biomphalaria glabrata* snails by light induction. Details regarding the methods used for the maintenance of both *S. mansoni* and *B. glabrata* cultures was as described in Salter et al., J. Biol. Chem. 275: 38667–38673 (2000). A total of 50–100 cercariae in 100 μL distilled water were collected and placed in COSTAR 96-well vinyl assay plates (COSTAR Corp., Acton, Mass.). Stock solutions of compounds 1–11, including 1a and 2a, were prepared by dissolving 1 mg of test compound in 100 μL of DMASO and 19.9 mL of distilled water. The stock solution was further diluted as needed and 100 μL aliquots were added to each well. Cercariae mobility (that is, tail movement and swimming behavior) was observed under a dissecting microscope. Viability of the cercariae was determined by removing the test compounds after about ten hours and replacing it with fresh water. Recovery from exposure to the test compounds was assessed after 24 hours.

The schistosomula assays were performed as follows. Schistosomula were prepared from *S. mansoni* cercariae by shearing the tails and incubating the organisms for two days in RPMI-1640 media containing penicillin and streptomycin and fetal bovine serum in flat-bottomed COSTAR 96-well CELL CULTURE CLUSTER tissue culture plates. Test compounds prepared as above were added to the media and the schistosomula were observed for changes in movement, feeding, and viability.

The adult assays were performed as follows. Adult worms were perfused from Syrian Golden hamsters as described in Davies et al., Science 294: 1358–1361 (2001). Twenty male and female adult worms were cultured in 24-well FALCON plates at 37° C. in one mL of RPMI-1640 media supplemented with 2 g/L glucose, 0.3 g/L L-glutamate, and 2.0 g/L NaHCO₃, 15% heat-inactivated fetal bovine serum, 1× penicillin/streptomycin, and 15 μL of hamster red blood cells which had been washed with RPMI-1640 medium. Five μL aliquots of the test compounds in DMSO (prepared as above) or DMSO control were added to each well. The movement, feeding, and viability of the adult worms were monitored for 24 hours. Afterwards, the media were removed and replaced with fresh media to which the test compounds or DMSO had been added and the adult worms observed for another 24 hours. Finally, the media were again removed and replaced with fresh media without the test compounds or DMSO and the recovery of the adult worms was monitored for another 24 hours.

Figure 6:
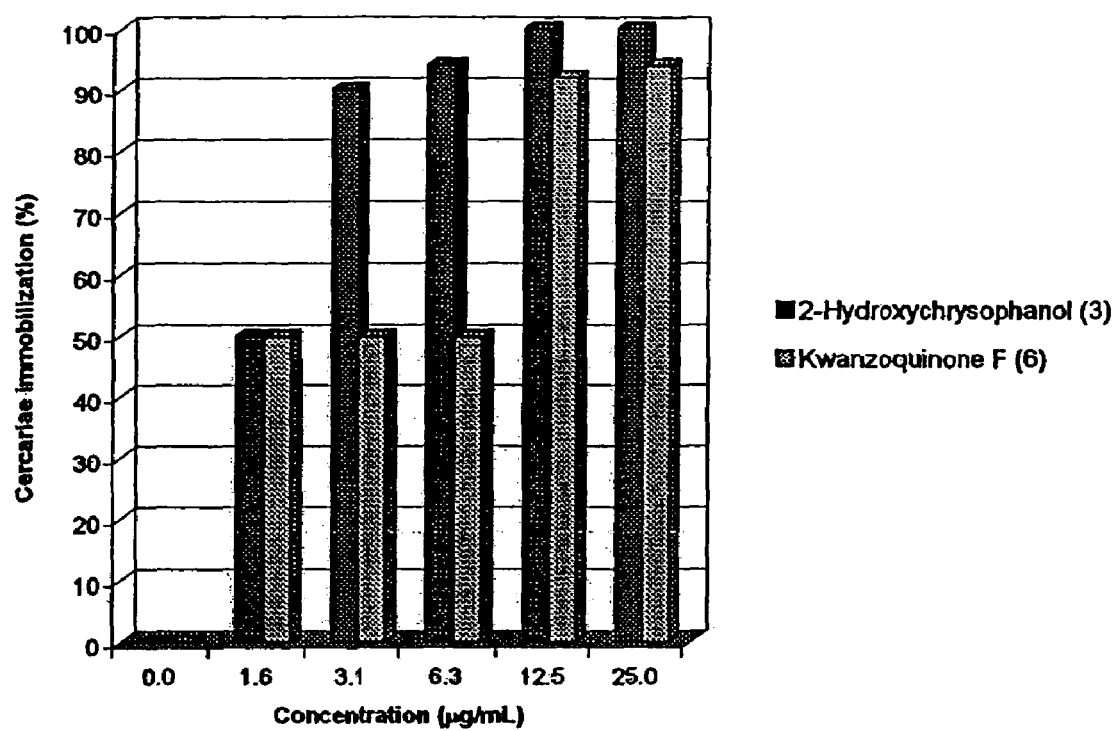
FIG. 6 shows the dose response effect of compound 3 (2-hydroxychrysophanol) and compound 6 (kwanzoquinone E) on *S. mansoni* cercariae mobility. Mobility was accessed bases on the movement and swimming behavior of the invasive aquatic larval stage.
Figure 7:
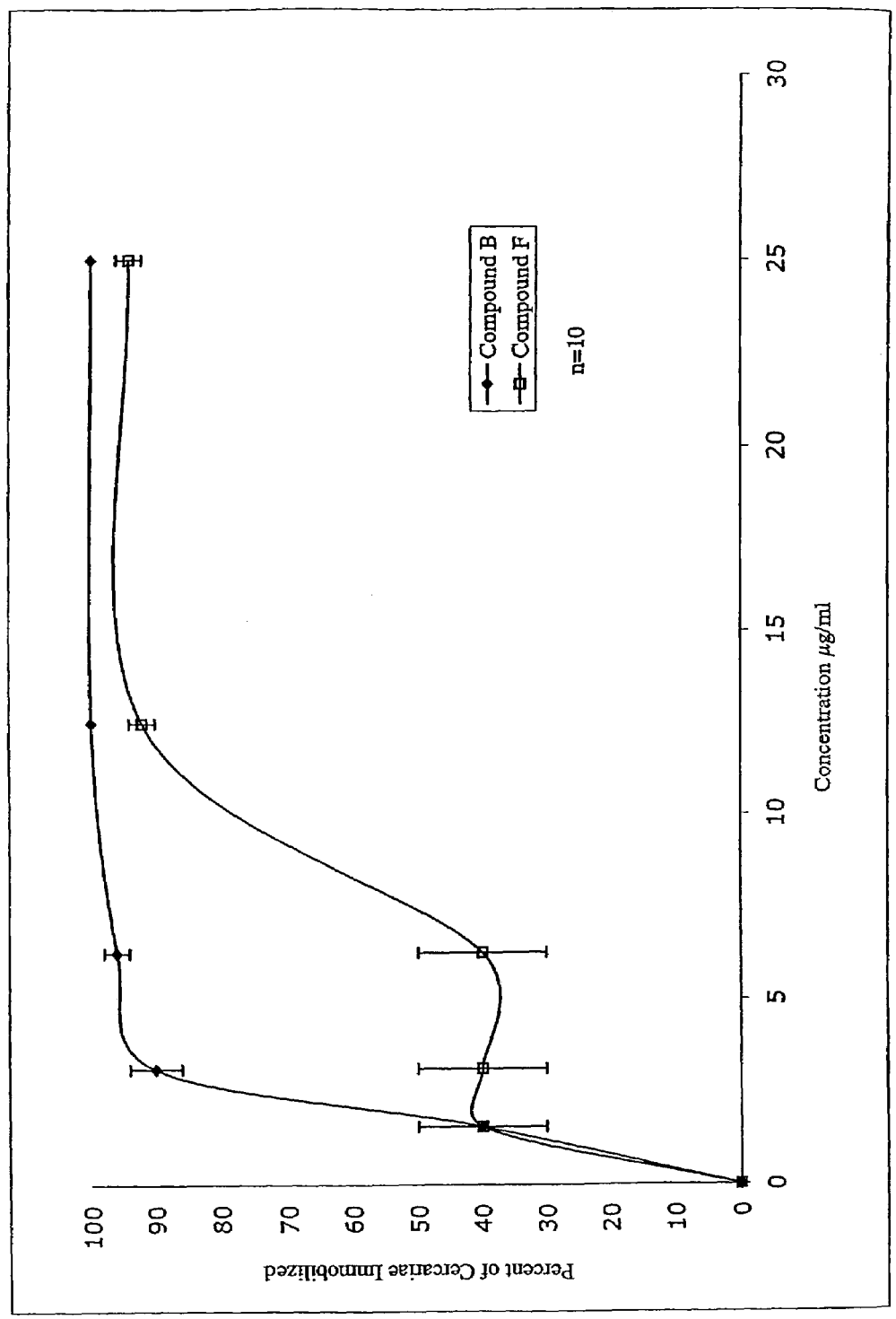
FIG. 7 is a graph showing the percent inhibition of mobilization of cercariae as a function of concentration of compounds 3 (B) and 6 (F).

At a concentration of 25 μg/mL, compounds 3 (2-hydroxychrysophanol) and 6 (kwanzoquinone E) exhibited significant activity by completely immobilizing all cercariae within 15 seconds and 14 minutes, respectively. The dose effect of these compounds is shown in Table 5 and FIGS. 6 and 7.

TABLE 5

| Concentration | Percent of Cercariae Immobilized | | | |
|---|---|---|---|---|
| (μg/mL) | Compound 3 | Error | Compound 6 | Error |
| 0 | 0 | 0 | 0 | 0 |
| 1.56 | 40 | 10 | 40 | 10 |
| 3.125 | 90 | 4 | 40 | 10 |
| 6.25 | 96 | 2 | 40 | 10 |
| 12.5 | 100 | 0 | 92 | 2 |
| 25 | 100 | 0 | 94 | 2 |

Total of 10 assays for each compound and 10 minutes per assay.

The potency of compound 3 was not diminished even when diluted to a concentration of 3.1 μg/mL. After 30 minutes of exposure to the test compounds, the solution containing the test compounds was removed and replaced with fresh media. Cercariae treated with compound 3 exhibited 50% mortality after 24 hours while those exposed to compound 6 were all dead. None of the other compounds isolated from *H. fulva* roots, including glycosides of compounds 3 and 6, compounds 4 and 7, respectively, exhibited any activity at 25 μg/mL. The adult worms were also immobilized within 16 hours by compounds 3 and 6 at 50 μg/mL. Following removal of the compounds, 35% and 55% of the adults exposed to compounds 3 and 6, respectively, were dead. In contrast to the effects on the cercariae and adults, the intermediate schistosomula stage was refractory to all compounds at 35 μg/mL.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. An antihelminthic composition which comprises:
    (a) at least one anthraquinone of the formula:

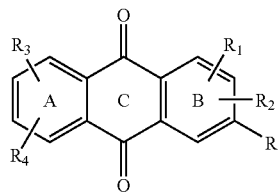

wherein $R_1$, $R_2$, $R_3$, and $R_4$ are selected from the group consisting of hydrogen, hydroxy, halogen, $R_3$ or $R_4$ is methyl, $R_1$ acetoxy, O-β-D-glucopyranoside, and $R_2$ -O-malonyl-(1→6 O-β-D-glucopyranoside groups, which provides antihelminthic activity, R is selected from the group consisting of methyl, hydroxy, hydroxymethyl, COOH, and methyl-O-β-D-glucopyranoside groups, and the halogen is selected from the group consisting of I, F, Br, and Cl, but not 1,2,8-trihydroxy-3-methyl anthraquinone or 1,8-hydroxy-3-R-anthraquinone where R is methyl, hydroxyl, hydroxymethyl or COOH; and
    (b) a pharmaceutically acceptable carrier, wherein the composition contains between about 1 and 1,000 micrograms of the anthraquinone per milliliter or gram of the carrier.

2. An antihelminthic composition which comprises:
    (a) at least one anthraquinone of the formula:

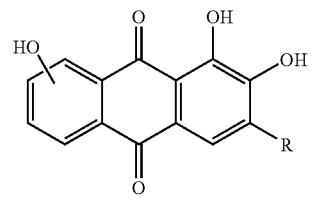

wherein R is selected from the group consisting of hydroxymethyl, COOH, and methyl-O-β-D-glucopyranoside groups; and
    (b) a pharmaceutically acceptable carrier, wherein the composition contains between about 1 and 1,000 micrograms of the anthraquinone per milliliter or gram of the carrier.

3. An antihelminthic composition which comprises:
    (a) at least one anthraquinone selected from the group consisting of 1-hydroxy-2-acetyl-3,6-methyl anthraquinone, 2-acetyl-3,6methyl anthraquinone monoacetate, 1-hydroxy-2-acetyl-3,7-methyl anthraquinone, 2-acetyl -3,7-methyl anthraquinone monoacetate, 1,8dihydroxy-2-O-C-D-glucopyranoside anthraquinone, 1,2,8-trihydroxy-3-hydroxymethyl anthraquinone, and 1,8-dihydroxy-3-carboxy anthraquinone; and
    (b) a pharmaceutically acceptable carrier, wherein the composition contains between about 1 and 1,000 micrograms of the anthraquinone per milliliter or gram of the carrier.

4. An isolated and purified anthraquinone which has the formula:

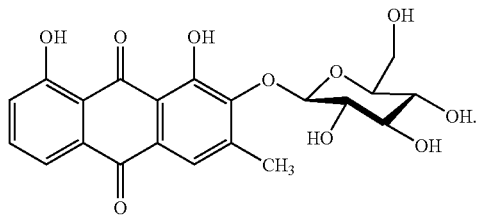

5. An isolated and purified anthraquinone which has the formula:
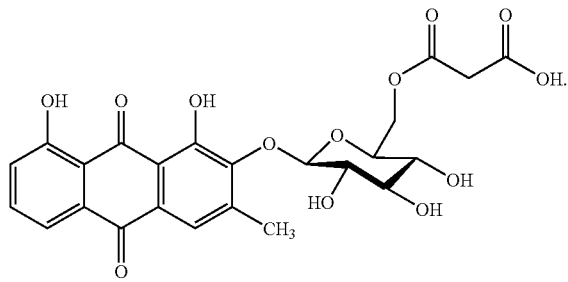
6. An isolated and purified anthraquinone which has the formula:
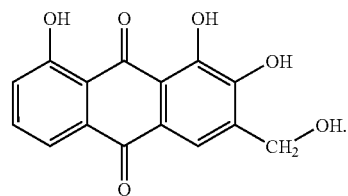
7. An isolated and purified anthraquinone which has the formula:
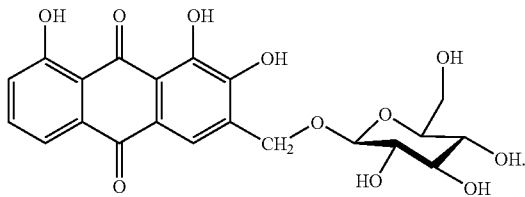
8. An isolated and purified anthraquinone which has the formula:
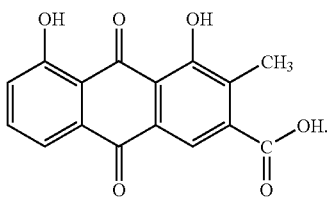
* * * * *

UNITED STATES PATENT AND TRADEMARK OFFICE
CERTIFICATE OF CORRECTION

PATENT NO.       : 7,132,403 B2
APPLICATION NO. : 10/761071
DATED            : November 7, 2006
INVENTOR(S)      : Robert H. Cichewicz, Muraleedharan G. Nair and James H. McKerrow It is certified that error appears in the above-identified patent and that said Letters Patent is hereby corrected as shown below:

Column 25, line 63, "UV max (EtOH)" should be --UV $\lambda_{max}$ (EtOH) --

Column 26, line 46, "C NMR" should be --$^{13}$C NMR--

Column 27, line 64, "1.27.3 (d, C–6) " should be --127.3 (d, C–6) --

Signed and Sealed this

Twelfth Day of June, 2007

JON W. DUDAS
*Director of the United States Patent and Trademark Office*